United States Patent
Kanrar et al.

(10) Patent No.: US 11,434,529 B2
(45) Date of Patent: Sep. 6, 2022

(54) PCR ASSAYS FOR SPECIFIC DETECTION OF ENTEROCYTOZOON HEPATOPENAEI

(71) Applicant: Arizona Board of Regents on Behalf of the University of Arizona, Tucson, AZ (US)

(72) Inventors: Siddhartha Kanrar, Tucson, AZ (US); Arun Dhar, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 22 days.

(21) Appl. No.: 16/798,283

(22) Filed: Feb. 21, 2020

(65) Prior Publication Data
US 2020/0270673 A1   Aug. 27, 2020

Related U.S. Application Data

(60) Provisional application No. 62/808,701, filed on Feb. 21, 2019.

(51) Int. Cl.
*C12Q 1/686* (2018.01)
*C12Q 1/04* (2006.01)

(52) U.S. Cl.
CPC .............. *C12Q 1/686* (2013.01); *C12Q 1/04* (2013.01); *C12Q 2561/113* (2013.01)

(58) Field of Classification Search
CPC .... C12Q 1/04; C12Q 1/686; C12Q 2561/113; C12Q 1/6895
See application file for complete search history.

(56) References Cited

PUBLICATIONS

Jaroenlak et al., "A Nested PCR Assay to Avoid False Positive Detection of the Microsporidian Enterocytozoon hepatopenaei (EHP) in Environmental Samples in Shrimp Farms," PLoS One, November, vol. 11, No. 11, e06166320, pp. 1-15. (Year: 2016).*
Somchai et al., "Use of microalgae *Chlamydomonas reinhardtii* for production of double-stranded RNA against shrimp virus," Aquaculture Reports, March, vol. 3, pp. 178-183. (Year: 2016).*
Liu et al., "Quantitative detection method of Enterocytozoon hepatopenaei using TaqMan probe real-time PCR," Journal of Invertebrate Pathology, December, vol. 151, pp. 191-196. (Year: 2017).*
Verweij et al., "Multiplexdetection of *Enterocytozoon bieneusi* and *Enchephalitozoon* spp. in fecal samples using real-time PCR," Diagnostic Microbiology and Infectious Disease, vol. 57, pp. 163-167. (Year: 2007).*
Fronhoffs, et al., A method for the rapid construction of cRNA standard curves in quantitative real-time reverse transcription polymerase chain reaction, Mol. Cell. Probes, vol. 16, pp. 99-110, Accepted for Publication Jan. 3, 2002.
Thitamadee, et al., "Review of current disease threats for cultivated penaeid shrimp in Asia," Aquaculture, vol. 452, pp. 69-87, Available online: Oct. 23, 2015.
Tang, et al., "Development of in situ hybridization and PCR assays for the detection of Enterocytozoon hepatopenaei (EHP), a microsporidian parasite infecting penaeid shrimp," J. Invertebr. Pathol., vol. 130, pp. 37-41, 2015.
Michael W. Pfaffl, "Relative quantification" pp. 63-82 in Real-Time PCR ed. T. Dorak., Published by International University, 2007.

* cited by examiner

*Primary Examiner* — Young J Kim
(74) *Attorney, Agent, or Firm* — Carin R. Miller, Esq.; Johnson, Marcou, Isaacs & Nix, LLC

(57) ABSTRACT

Described herein are assays and kits capable of specifically detecting *Enterocytozoon hepatopenaei* (EHP) in a nucleic acid sample. In some embodiments, the nucleic acid sample is obtained from shrimp tissue, shrimp feed, or a feed ingredient.

12 Claims, 12 Drawing Sheets

Specification includes a Sequence Listing.

SEQUENCE LISTING

```
<160> NUMBER OF SEQ ID NOS: 7

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 1
gcctgagaga tggctcccac gt                                             22

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 2
gcgtactatc cccagagccc ga                                             22

<210> SEQ ID NO 3
<211> LENGTH: 458
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t

<400> SEQUENCE: 3
aattcagcaa cagtcccgag atgcctgctt ggcgggcatc ggtttactgg cgtggaaact      60
acagcgggta tcgtaatcac tttcggatcc cccagcccgc cttggatccn cagactcgtn     120
caagttgcat ccctttcgcc ntgcgtcagt ccaggcgggg tcttggtcat ttcatctctc     180
gcccgcctat actatgcact ctgcccgttc cgccatcctt agnaaaccct gcaccnttga     240
```

```
ccggtgccct tcaattgcat atacaactac ggactttta actgcagcat ccaccataga      300
cactcttgga gtcggtatta ccgcggctgc tggcacnaaa cttgccctcc aatactcaaa      360
gcacttgttt actgtgccct ctaatctacg tctcataact gcctcctcac caaagagtgg      420 gcaatttcg cgcctgctgc cgtccttgga ngtgggag                              458
```

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4

```
atttgacgat cctggtttgg                                                  20
```

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5

```
tggccatcga tgtgattatg                                                  20
```

<210> SEQ ID NO 6
<211> LENGTH: 897
<212> TYPE: DNA
<213> ORGANISM: Enterocytozoon hepatopenaei

<400> SEQUENCE: 6

```
atttgacgat cctggtttgg tcaattggtt tgagttgatt tcatttatta tggctatttt      60
tattttcaag atttttacaa aaatttgtcg taagtacggg gtaaacaaag gggtagactt      120
atacatgata tcttgtgcat cgattttgg cggatttatt gctcttatcg catttgacag      180
atttgttttt tccacgaaag gtgggtattg tgaagaatta tttaatggaa atttggcatc      240
tataagacac gtcagcatat ttttgcgtcc ggcaaaatta ctgaatttat ttttatgac       300 aattttttca gtgtttctgg aagtttcttc ttcatttttg atatcagtca tatttatgac      360
atatctgtca tcaaacatta cacgcagca aaatcaaaga tatttattcc ccattctttt      420
tggtgctaat atggcgttgt ttttctctgt ttatgctgtt aaattgacag tgaagcaaat     480
caacaagttt tcggtagcat caacttcctg ggtgttttac tcaatcttta tttttgatgtt    540 gattcttcta tacggtatca ttttggtct taaaaaggta cttgattatg aatggaaaaa      600
acctctttat attggtcagc ctattcttgg taatttacca caaaaaaata aaaaagcaga     660
aaataaaact tctttcttag aagctttaaa gacaatttt aaaacaaat ggttgatggg      720 aatatgcacg cttgctttat tttataatat ttcagtgtt atagtcacat cacaatcatt     780 ttatcatat gcagcacatg cagattatta tgctgcaaat cctttgatga ttaataaacc     840
tggtttcatt ccaacaaaat caaatgtatc tgttttttac aagagcacag aatgcat        897
```

<210> SEQ ID NO 7
<211> LENGTH: 1803
<212> TYPE: DNA
<213> ORGANISM: Enterocytozoon hepatopenaei

<400> SEQUENCE: 7

```
atgagaaatg aaaattttgg taaaggagat acttttaaag aagattcaaa gaagttaatg     60
ggcgagtcct cttactatca aaacaaagaa ctatttacaa atggatctag aaatcacatt    120
tttactgcta caagcacagt agaaaaaaca gtaaacgtcg atgaaaaagt aatgagtttt    180
gaagaatatg aagaggaggt taaaaaagta aaaaacacaa aattgggaag ttttttgacc    240
atcataagat cagaatacaa acgagtattt ctttcaatca catgctattt tgttgtgtgt    300
tttctgtatt cttttgttag acagtttaga gatgtgatag tgtttgacgt atttgacgat    360
cctggtttgg tcaattggtt tgagttgatt tcatttatta tggctatttt tattttcaag    420
attttacaa aaatttgtcg taagtacggg gtaaacaaag gggtagactt atacatgata    480
tcttgtgcat cgattttgg cggatttatt gctcttatcg catttgacag atttgttttt    540
tccacgaaag gtgggtattg tgaagaatta tttaatggaa atttggcatc tataagacac    600
gtcagcatat ttttgcgtcc ggcaaaatta ctgaatttat tttttatgac aattttttca    660
gtgtttctgg aagtttcttc ttcatttttg atatcagtca tatttatgac atatctgtca    720
tcaaacatta cacacgagca aaatcaaaga tatttattcc ccattctttt tggtgctaat    780
atggcgttgt ttttctctgt ttatgctgtt aaattgacag tgaagcaaat caacaagttt    840
tcggtagcat caacttcctg ggtgttttac tcaatcttta ttttgatgtt gattcttcta    900
tacggtatca ttttggtct taaaaaggta cttgattatg aatggaaaaa acctctttat    960
attggtcagc ctattcttgg taatttacca caaaaaaata aaaaagcaga aaataaaact   1020
tctttcttag aagctttaaa gacaattttt aaaacaaaat ggttgatggg aatatgcacg   1080
cttgctttat tttataatat ttctagtgtt atagtcacat cacaatcatt ttattcatat   1140
gcagcacatg cagattatta tgctgcaaat cctttgatga ttaataaacc tggtttcatt   1200
ccaacaaaat caaatgtatc tgttttttac aagagcacag aatgcataat cacatcgatg   1260
gccaccatga ttcttatgct tttaccggtg tttaaaaaga ttttgaaat ttttggtgtt    1320
ttgtcatttg gctcgattgt gatttttgg ccgattatca attttgctgt atgttatttt    1380
tttgcagcta taaattatcc ttttacaaac aatggtaaca ctattttatg caatcttggt   1440
atatcaaaaa ccaagccaaa ttttgaagct gaatcagcgc ttatttgtgc attaaacatc   1500
gcagcaaagg taagcaagta ttctttttat gacattatta agaaaagtgt ttcaagcaaa   1560
atagatccac aaaataaggt ttttttataaa ggcatttttg atgggataat gccaaaaaca   1620
ggaaagttat tttgcgtagc ttattttatt ttgatgacga gtatttttgaa caaaaatgat   1680
gtaagatatt tttcagcagt atcattgatt ttccttgtag ggatgggatc agttgcaatg   1740
tattctacaa ttttacttca taaagcatat aaaaaagcaa taaacaccaa taaatatctt   1800
taa                                                                 1803
```

PCR ASSAYS FOR SPECIFIC DETECTION OF ENTEROCYTOZOON HEPATOPENAEI

CROSS-REFERENCE TO RELATED APPLICATIONS

This application claims the benefit of and priority to co-pending U.S. Provisional Patent Application No. 62/808,701, filed on Feb. 21, 2019, entitled "PCR ASSAYS FOR SPECIFIC DETECTION OF ENTEROCYTOZOON HEPATOPENAEI," the contents of which is incorporated by reference herein in its entirety.

SEQUENCE LISTING

This application contains a sequence listing filed in electronic form as an ASCII.txt file entitled UAZ-0110US_ST25.txt, created on Feb. 20, 2020 and having a size of 6 kb. The content of the sequence listing is incorporated herein in its entirety.

TECHNICAL FIELD

The subject matter disclosed herein is generally directed to detecting and treating shrimp diseases.

BACKGROUND

Aquaculture farms, especially shrimp farms, is a rapidly growing market as they provide an abundant, cheap source of protein. The global shrimp market is currently valued at about $40 billion and is expected to increase to $68 billion by 2028. Of key concern to this market is aquaculture disease. EHP is a fungal disease that affects aquacultures primarily in South and Southeast Asia but has been recorded in Venezuela as well. EHP severely restricts shrimp growth, causes size variability in the population, and increases shrimp susceptibility to acute hepatopancreatic necrosis disease (AHPND) and septic hepatopancreatic necrosis (SHPN). Currently, control of EHP disease is through early detection and prevention, which requires a reliable method for detecting EHP in a variety of samples. As such there exists a need for reliable detection methods for EHP in shrimp.

Citation or identification of any document in this application is not an admission that such a document is available as prior art to the present invention.

SUMMARY

In certain example embodiments, described herein are polymerase chain reaction (PCR) assays capable of specifically detecting *Enterocytozoon hepatopenaei* (EHP) in a nucleic acid sample, the assay including: specifically amplifying a gene fragment selected from a shrimp ATP-ADP carrier protein gene an EHP spore gene, or both, and optionally an EHP spore wall gene using a polymerase chain reaction (PCR) method, wherein the step of specifically amplifying includes: contacting a nucleic acid sample obtained from one or more shrimp, shrimp feed, or shrimp feed ingredient with one or more first primer pairs, wherein each of the one or more first primer pairs are configured to specifically amplify one gene fragment from a gene selected from a shrimp ATP-ADP carrier protein gene an EHP spore gene, or both, and optionally an EHP spore wall gene, wherein each of the one or more first primer pairs has a first oligonucleotide primer and a second oligonucleotide primer, and wherein the each of the one or more first primer pairs are configured to specifically amplify a different gene fragment, wherein the first oligonucleotide primer of each of the one or more first primer pairs is a forward direction oligonucleotide primer adapted for PCR amplification of the one gene fragment and specifically binds the gene, and wherein the second oligonucleotide primer of each of the one or more first primer pairs is a reverse direction oligonucleotide primer adapted for PCR amplification of the one gene fragment and specifically binds the gene at a different location on the gene then the first oligonucleotide primer, optionally contacting the nucleic acid sample with a second primer pair having a third oligonucleotide primer and a fourth oligonucleotide primer, wherein the third oligonucleotide primer is a forward direction oligonucleotide primer adapted for PCR amplification of a fragment of a control gene, wherein the fourth oligonucleotide primer is a reverse direction oligonucleotide primer adapted for PCR amplification of a fragment of the control gene; detecting the presence or absence of an amplified double stranded DNA fragment of the shrimp ATP-ADP carrier protein gene, the EHP spore gene, or both, and optionally the EHP spore wall gene in the nucleic acid sample; and optionally detecting the presence or absence of an amplified double stranded DNA fragment of the control gene in the nucleic acid sample.

In certain example embodiments, the PCR method is a real-time PCR method and wherein amplifying further includes contacting the nucleic acid sample with one or more first oligonucleotide probes adapted for real-time PCR amplification and detection, wherein each first oligonucleotide probe is configured to bind a different gene fragment selected from an ATP-ADP carrier protein gene fragment or a EHP spore gene fragment, and optionally an EHP spore wall gene, wherein each of the one or more first oligonucleotide probes specifically binds a region of the gene DNA fragment that is between a binding region of the first oligonucleotide primer and a binding region of the second oligonucleotide primer in the gene, and wherein each of the one or more first oligonucleotide probes is coupled to a fluorophore and a quencher molecule; and optionally contacting the nucleic acid sample with a second oligonucleotide probe adapted for real-time PCR amplification and detection, wherein the second oligonucleotide probe specifically binds a region of the control gene that is between a binding region of the third oligonucleotide primer and a binding region the fourth oligonucleotide primer in the control gene, and wherein the second oligonucleotide probe is coupled to a fluorophore and a quencher molecule.

In certain example embodiments, the control gene is beta actin or shrimp 18S rRNA.

In certain example embodiments, the fluorophore of the one or more first oligonucleotide probes and at the second oligonucleotide probe are responsive to double stranded DNA and are capable of producing a detectable fluorescence being upon activation during the step of amplifying in response to double stranded DNA production during amplifying.

In certain example embodiments, detection occurs during the step of amplifying.

In certain example embodiments, amplifying further comprises contacting the amplified double stranded DNA fragment of the ATP-ADP carrier protein gene, the EHP spore gene, or both, and optionally the amplified double stranded DNA fragment of the EHP spore wall gene with a detectable dye molecule that binds double stranded DNA and optionally contacting the amplified double stranded DNA fragment of the control gene with a detectable dye molecule that binds double stranded DNA.

In certain example embodiments, contacting the amplified double stranded DNA fragment of the ATP-ADP carrier protein gene, the EHP spore gene, or the EHP spore wall gene with a detectable dye molecule that binds double stranded DNA occurs during the step of amplifying.

In certain example embodiments, amplifying the ATP-ADP carrier protein gene, the EHP spore gene, or both, and optionally amplifying the EHP spore wall gene and amplifying the control gene is carried out in the same PCR reaction.

In certain example embodiments, amplifying the ATP-ADP carrier protein gene, the EHP spore gene, or both, and optionally amplifying the EHP spore wall gene and the amplifying the control gene is carried out in the different PCR reactions.

In certain example embodiments, the fluorophore of at least one of the first oligonucleotide probes is different from the fluorophore of the second oligonucleotide probe.

In certain example embodiments, the first oligonucleotide primer of at least one of the one or more first primer pairs has a sequence according to SEQ ID NO: 4, the second oligonucleotide primer of at least one of the one or more second primer pairs has a sequence according to SEQ ID NO: 5; or both.

In certain example embodiments, there is no detectable non-specific amplification of a PCR product.

In certain example embodiments, the assay does not detect a non-EHP organism selected from the group consisting of: *Enterocytospora artemiae*, acute hepatopancreatic necrosis disease (AHPND), infectious hypodermal and hematopoietic necrosis virus (IHHNV), necrotizing hepatopancreatitis (NHP), white spot syndrome virus (WSSV), infectious myonecrosis virus (IMNV), *Penaeus vannamei* nodavirus (PvNV), Taura syndrome virus (TSV), yellowhead disease (YHV), and combinations thereof.

In certain example embodiments, described herein are kits for specifically detecting *Enterocytozoon hepatopenaei* (EHP) in a nucleic acid sample via a PCR method, including one or more first primer pairs adapted for the PCR method, wherein each of the one or more first primer pairs comprises a first oligonucleotide primer and a second oligonucleotide primer, wherein each of the one or more first primer pairs are configured to specifically amplify one gene fragment from a gene selected from a shrimp ATP-ADP carrier protein gene an EHP spore gene, or both, and optionally an EHP spore wall gene, and wherein each of the one or more first primer pairs includes a first oligonucleotide primer and a second oligonucleotide primer, and wherein the each of the one or more first primer pairs are configured to specifically amplify a different gene fragment, wherein the first oligonucleotide primer of each of the one or more first primer pairs is a forward direction oligonucleotide primer adapted for PCR amplification of the one gene fragment and specifically binds the gene, and wherein the second oligonucleotide primer of each of the one or more first primer pairs is a reverse direction oligonucleotide primer adapted for PCR amplification of the one gene fragment and specifically binds the gene at a different location on the gene then the first oligonucleotide primer; and optionally further comprising a second primer pair adapted for the PCR method, wherein the second primer pair comprises a third oligonucleotide primer and a fourth oligonucleotide primer, wherein the third oligonucleotide primer is a forward direction oligonucleotide primer adapted for amplification of a fragment of a control gene with the fourth oligonucleotide primer and specifically binds a region of the control gene, and wherein the fourth oligonucleotide primer is a reverse direction oligonucleotide primer adapted for amplification of a fragment of the control gene with the third oligonucleotide primer and specifically binds a region of the control gene that is different that the region of the control gene that the third oligonucleotide primer specifically binds.

In certain example embodiments, the kit further includes an amount of
a) a detectable dye molecule that binds double stranded DNA;
b) one or more first oligonucleotide probes adapted for real-time PCR,
   wherein each first oligonucleotide probe is configured to bind a different gene fragment selected from an ATP-ADP carrier protein gene fragment or a EHP spore gene fragment, and optionally an EHP spore wall gene,
   wherein each of the one or more first oligonucleotide probes specifically binds a region of the gene DNA fragment that is between a binding region of the first oligonucleotide primer and a binding region of the second oligonucleotide primer in the gene, and
   wherein the first oligonucleotide probe is coupled to a fluorophore and a quencher molecule;
c) a second oligonucleotide probe adapted for real-time PCR
   wherein the second oligonucleotide probe specifically binds a region of the control gene that is between a binding region of the third oligonucleotide primer and a binding region the fourth oligonucleotide primer, and
   wherein the second oligonucleotide probe is coupled to a fluorophore and a quencher molecule; or
d) a combination thereof.

In certain example embodiments, the detectable dye molecule that binds double stranded DNA is a cyanine dye.

In certain example embodiments, the detectable dye molecule that binds double stranded DNA is N',N'-dimethyl-N-[4-[(E)-(3-methyl-1,3-benzothiazol-2-ylidene)methyl]-1-phenylquinolin-1-ium-2-yl]-N-propylpropane-1,3-diamine and variants thereof.

In certain example embodiments, the fluorophore of at least one of the first oligonucleotide probes is different from the fluorophore of at least one of the second oligonucleotide probes.

In certain example embodiments, the first oligonucleotide primer of at least one of the one or more first primer pairs has a sequence according to SEQ ID NO: 4, the second oligonucleotide primer of at least one of the one or more second primer pairs has a sequence according to SEQ ID NO: 5; or both.

In certain example embodiments, the control gene is beta actin or shrimp 18S rRNA.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

As shown in FIG. 1, the frozen Artemia sample is negative for EHP, but the PCR test using 18S rDNA primers resulted in a false-positive result.

FIGS. 3A and 3B can demonstrate specific amplification of EHP from infected samples without detectable non-specific amplification (as observed by no detectable detection in EHP-negative samples (frozen Artemia)).

FIGS. 4A and 4B show results from different samples tested by PCR 1) with EHP510 PCR and 2) ATP-900 PCR M—Invitrogen 1 kb DNA ladder, Different feeds (17-393, 17-554, 17-295, 17-234, 17-240, 17-202, 17-199, 17-279), frozen Artemia (17-293, 17-628), Yeast—Baker's yeast DNA, E. coli—Escherichia coli DNA, SPF—Specific pathogen free, NTC—Non template control, Inf-20 and Inf-1—EHP-infected shrimp, Inf-19 and Inf-2—EHP-infected shrimp, +C—Positive control.

FIG. 6A shows a graph that can demonstrate a representative qPCR standard curve. FIG. 6B shows a graph that can demonstrate results from a qPCR assay capable of detecting common shrimp diseases. 1: plasmid DNA, 2: EHP-infected tissue, 3-10: AHPND, IHHNV, NHP, WSSV, IMNV, PvNV, TSV, YHV, SPF, NTC. FIG. 6C shows a graph that can demonstrate screening of putative EHP-infected P. vannamei post-larvae. 1: plasmid DNA, Epl-1-30—EHP-infected shrimp, Specific Pathogen Free (SPF) shrimp.

Figure 1:
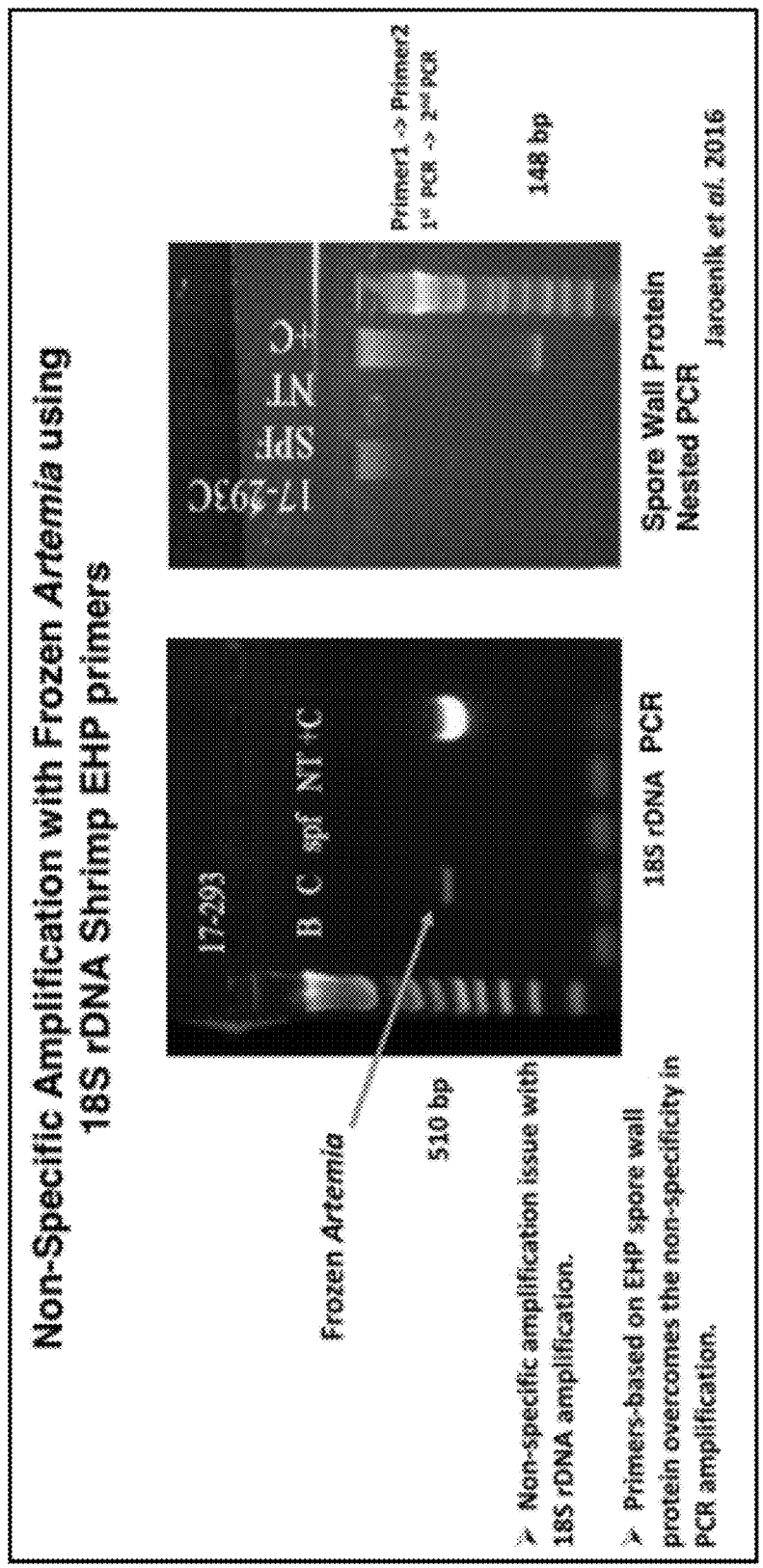
FIG. 1—Images of gels demonstrating PCR results using 18s rDNA shrimp primers (SEQ ID NOs. 1 and 2) and can demonstrate a false positive result for EHP when using the conventional primers to detect EHP.

The figures herein are for illustrative purposes only and are not necessarily drawn to scale.

DETAILED DESCRIPTION OF THE EXAMPLE EMBODIMENTS

Before the present disclosure is described in greater detail, it is to be understood that this disclosure is not limited to particular embodiments described, and as such may, of course, vary. It is also to be understood that the terminology used herein is for the purpose of describing particular embodiments only and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosed invention. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

As used herein, a "biological sample" may contain whole cells and/or live cells and/or cell debris. The biological sample may contain (or be derived from) a "bodily fluid". Bodily fluids can include, without limitation, amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a biological non-human animal or human, which can be a vertebrate or invertebrate. In some embodiments, the subject is a vertebrate, preferably a mammal, more preferably a human. Mammals include, but are not limited to, murines, simians, humans, farm animals, sport animals, and pets. In some embodiments, the subject is a non-human animal invertebrate including, but not limited to, a crustacean, e.g. a crab, lobster, or shrimp. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein, "control" refers to an alternative subject or sample used in an experiment for comparison purpose and included to minimize or distinguish the effect of variables other than an independent variable.

As used herein with reference to the relationship between DNA, cDNA, cRNA, RNA, protein/peptides, and the like "corresponding to" refers to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "deoxyribonucleic acid (DNA)" and "ribonucleic acid (RNA)" generally refers to any polyribonucleotide or polydeoxyribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "DNA molecule" can include nucleic acids/polynucleotides that are made of DNA.

As used herein, the term "encode" refers to principle that DNA can be transcribed into RNA, which can then be translated into amino acid sequences that can form proteins.

As used herein, "gene" refers to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA.

As used herein, "identity," refers to a relationship between two or more nucleotide or polypeptide sequences, as determined by comparing the sequences. In the art, "identity" can also refer to the degree of sequence relatedness between nucleotide or polypeptide sequences as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M, and Griffin, H. G., Eds., Humana Press, New Jersey, 1994; Sequence Analysis in Molecular Biology, von Heinje, G., Academic Press, 1987; and Sequence Analysis Primer, Gribskov, M and Devereux, J., Eds., M Stockton Press, New York, 1991; and Carillo, H., and Lipman, D., SIAM J. Applied Math. 1988, 48:1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48:443-453,) algorithm (e.g., NBLAST, and XBLAST). The default parameters are used to determine the identity for the polypeptides of the present disclosure, unless stated otherwise. Methods of determining identity can also be used to determine complementarity.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "nucleic acid," "nucleotide sequence," and "polynucleotide" are used interchangeably herein and generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein can refer to triple-stranded regions comprising RNA or DNA or both RNA and DNA. The strands in such regions can be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide as used herein can include DNAs or RNAs as described herein that contain one or more modified bases. Thus, DNAs or RNAs including unusual bases, such as inosine, or modified bases, such as tritylated bases, to name just two examples, are polynucleotides as the term is used herein. "Polynucleotide", "nucleotide sequences" and "nucleic acids" also includes PNAs (peptide nucleic acids), phosphonothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotides" as that term is intended herein. As used herein, "nucleic acid sequence" and "oligonucleotide" also encompasses a nucleic acid and polynucleotide as defined elsewhere herein.

As used herein, "positive control" can refer to a "control" that is designed to produce the desired result, provided that all reagents are functioning properly and that the experiment is properly conducted.

As used herein, the term "specific binding" refers to covalent or non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include primer-polynucleotide interaction, aptamer-aptamer target interactions, antibody-antigen interactions, avidin-biotin interactions, ligand-receptor interactions, metal-chelate interactions, hybridization between complementary nucleic acids, etc.

As used herein, "specifically detecting" refers to detecting a target polynucleotide predominantly while not substantially detecting non-target sequences at a level that detection (if any) of non-target sequences is undetectable or below the limit of detection or within background level of amplification for the particular method used.

As used herein, "specifically amplifying" refers to amplifying a target polynucleotide predominantly while not substantially amplifying to non-target sequences to a level that amplification (if any) of non-target sequences is undetectable or below the limit of detection or within background level of amplification for the particular method used.

As used herein, the term of art "primer" refers to a nucleic acid sequence that provides a starting point for DNA or RNA synthesis. They can be used in an in vitro reaction, such as in a DNA amplification method such as the polymerase chain reaction, a sequencing method, or in vitro transcription method. Primers are generally short (e.g. about 1-50 nucleotides) sequences, and are typically oligonucleotides. "Primer pair" refers to two primers that are designed to work together in a DNA synthesis and/or amplification method and can define the boundaries of a DNA (or RNA) being synthesized. Typically, there is a forward and reverse primer in a primer pair. Primers have complimentary sequences to a target polynucleotide. Generally, primers have a high degree of complementarity to a region in a target polynucleotide. This region is also referred to in the art as a "primer binding site." The degree of complementarity between primer to a target polynucleotide can range from about 80-100%, such as 80 to 81, 82, 83, 84, 85, 86, 87, 88, 89, 90, 91, 92, 93, 94, 95, 96, 97, 98, 99, or 100%. The degree of complementarity between a primer to a target polynucleotide can be 81, 82, 83, 84, 85, 86, 87, 88, 89, 90, 91, 92, 93, 94, 95, 96, 97, 98, 99, or 100%.

As used herein, the term of art "amplification" refers to the production of additional polynucleotides via a method employing one or more primers and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. An exemplary amplification method is a PCR method.

As used herein, "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. In some aspects a gene can be transcribed to yield non-coding RNA, such that the RNA has a functional role to play in the organism.

Embodiments of the present disclosure will employ, unless otherwise indicated, techniques of molecular biology, parasitology, virology, marine biology microbiology, organic chemistry, biochemistry, physiology, cell biology, and the like, which are within the skill of the art. Such techniques are explained fully in the literature.

All publications, published patent documents, and patent applications cited herein are hereby incorporated by reference to the same extent as though each individual publication, published patent document, or patent application was specifically and individually indicated as being incorporated by reference.

Overview

Hepatopancreatic microsporidosis, caused by *Enterocytozoon hepatopenaei* (EHP), is an emerging disease in shrimp aquaculture. The disease was originally described in 2003 in *Penaeus monodon* (also known as the "Tiger Shrimp") cultured in Thailand. Since the initial report of this disease from Thailand, EHP has now been reported from several South and South East Asian countries including China, Indonesia, Malaysia, Vietnam, and India. EHP is diagnosed through H&E histology examination of hepatopancreatic tissue from suspected animals, in situ hybridization and PCR.

There is no known treatment for EHP and thus control comes from identifying and preventing infection and spread of infection by removal of infected animals. The PCR diagnosis of EHP is based on the amplification of 18S rDNA gene using the primers EHP-510F (SEQ ID NO: 1) and EHP-510R (SEQ ID NO: 2), which generates a 510 bp amplicon. Despite this PCR assay being the current standard for PCR diagnosis of EHP, it has been observed that these primers and the resulting amplicon is non-specific for EHP and, in fact, may be indicative of a different microorganism.

Indeed, during routine screening of samples for EH, an approximately 510 bp amplicon was obtained for a frozen Artemia sample but not from dry Artemia cyst sample. Since EHP has not been reported from either dry cysts and frozen Artemia samples, the initial results need to be validated using a second set of primers targeting a gene other than 18s rRNA. As such, PCR amplification was carried out using EHP-specific primers based on the EHP spore wall gene. No EHP-specific amplicon was obtained for frozen Artemia samples. Due to the discrepancy in PCR amplification between 18s rRNA and spore wall amplification results, 510 bp amplicon from frozen Artemia was sequenced (SEQ ID NO: 3). The sequence analysis revealed that the 510 bp amplicon does not represent EHP of shrimp and instead showed about a 99% similarity to a different microsporidium, *Enterocytospora artemiae*, that infects Artemia. This indicated that the primers based on the 18S rRNA gene is not highly specific for the detection of EHP in shrimp, especially when frozen Artemia samples are screened, and alternative primers need to be developed for the specific PCR detection of EHP of shrimp.

With the limitations of current methods in mind, described herein are primers that can be used for the specific detection of EHP in shrimp. In some aspects the primer set(s) do not result in detectable non-specific amplification. The primers can be used in PCR-based detection assays for detection of EHP in shrimp, shrimp feed, and feed ingredients like frozen Artemia. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Assays to Specifically Detect EHP

As previously discussed, the current gold standard PCR assay relies on primers (SEQ ID NOs.: 1 and 2) to amplify a 510 bp amplicon. As shown in FIG. 1, the current primers that are the basis for the "gold" standard PCR assay for detection of EHP in shrimp are not specific for EHP. Indeed, these primers amplify other products that lead to inaccurate results.

Described herein are PCR-based assays that can be capable of specifically detecting and/or amplifying EHP from a nucleotide sample obtained from one or more shrimp, shrimp feed, and/or feed ingredients. In some embodiments, the sample is a water sample from a shrimp's environment. In some embodiments, the sample obtained is from hepatopancreas tissue and/or cells. Methods of harvesting, collecting, extracting and otherwise preparing an appropriate nucleic acid sample from shrimp, shrimp feed, and/or feed ingredients for analysis by polymerase chain reaction will be appreciated by one of ordinary skill in the art in view of this disclosure. The amount of sample can be any suitable non-zero amount. In some embodiments the amount of sample can range from 0.1-1.0 pg, ng, microgram, g, kg, pL, nL, microliter, mL, L or more, such as 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99 to/or 1.00 pg, ng, microgram, g, kg, pL, nL, microliter, mL, L or more.

DNA extraction from shrimp tissue, feed, and/or feed ingredient samples can be carried out using a commercial method. For example, DNA extraction can be carried out using a Maxwell® 16 Cell LEV DNA Purification Kit. Other suitable commercial reagents, kits, and methods will be appreciated by one of ordinary skill in the art in view of this description herein. The nucleic acid sample can contain, for example, genomic DNA, cDNA, and/or RNA.

After obtaining the nucleic acid sample, an ATP-ADP carrier protein gene and/or EHP spore gene, and/or EHP spore wall gene can be specifically amplified and/or detected by performing a PCR based assay. The PCR based-assay can be one step or multiple step PCR assay. The PCR based assay can employ an appropriate primer set to specifically amplify an amplicon specific to an ATP-ADP carrier protein gene, an EHP spore gene, or an EHP spore wall gene. The PCR based assay can also employ appropriate primer sets to amplify one or more reaction and assay control genes, such as a shrimp control (or housekeeping) gene (e.g. beta actin or 18S rRNA).

In certain example embodiments, described herein are polymerase chain reaction (PCR) assays capable of specifically detecting *Enterocytozoon hepatopenaei* (EHP) in a nucleic acid sample, the assay including: specifically amplifying a gene fragment selected from a shrimp ATP-ADP carrier protein gene an EHP spore gene, or both, and optionally an EHP spore wall gene using a polymerase chain reaction (PCR) method, wherein the step of specifically amplifying includes: contacting a nucleic acid sample obtained from one or more shrimp, shrimp feed, or shrimp feed ingredient with one or more first primer pairs, wherein each of the one or more first primer pairs are configured to specifically amplify one gene fragment from a gene selected from a shrimp ATP-ADP carrier protein gene an EHP spore gene, or both, and optionally an EHP spore wall gene, wherein each of the one or more first primer pairs has a first oligonucleotide primer and a second oligonucleotide primer, and wherein the each of the one or more first primer pairs are configured to specifically amplify a different gene fragment, wherein the first oligonucleotide primer of each of the one or more first primer pairs is a forward direction oligonucleotide primer adapted for PCR amplification of the one gene fragment and specifically binds the gene, and wherein the second oligonucleotide primer of each of the one or more first primer pairs is a reverse direction oligonucleotide primer adapted for PCR amplification of the one gene fragment and specifically binds the gene at a different location on the gene then the first oligonucleotide primer, optionally contacting the nucleic acid sample with a second primer pair having a third oligonucleotide primer and a fourth oligonucleotide primer, wherein the third oligonucleotide primer is a forward direction oligonucleotide primer adapted for PCR amplification of a fragment of a control gene, wherein the fourth oligonucleotide primer is a reverse direction oligonucleotide primer adapted for PCR amplification of a fragment of the control gene; detecting the presence or absence of an amplified double stranded DNA fragment of the shrimp ATP-ADP carrier protein gene, the EHP spore gene, or both, and optionally the EHP spore wall gene in the nucleic acid sample; and optionally detecting the presence or absence of an amplified double stranded DNA fragment of the control gene in the nucleic acid sample.

In certain example embodiments, the PCR method is a real-time PCR method and wherein amplifying further includes contacting the nucleic acid sample with one or more first oligonucleotide probes adapted for real-time PCR amplification and detection, wherein each first oligonucleotide probe is configured to bind a different gene fragment selected from an ATP-ADP carrier protein gene fragment or a EHP spore gene fragment, and optionally an EHP spore wall gene, wherein each of the one or more first oligonucleotide probes specifically binds a region of the gene DNA fragment that is between a binding region of the first oligonucleotide primer and a binding region of the second oligonucleotide primer in the gene, and wherein each of the one or more first oligonucleotide probes is coupled to a fluorophore and a quencher molecule; and optionally contacting the nucleic acid sample with a second oligonucleotide probe adapted for real-time PCR amplification and detection, wherein the second oligonucleotide probe specifically binds a region of the control gene that is between a binding region of the third oligonucleotide primer and a binding region the fourth oligonucleotide primer in the control gene, and wherein the second oligonucleotide probe is coupled to a fluorophore and a quencher molecule.

In certain example embodiments, the fluorophore of the one or more first oligonucleotide probes and at the second oligonucleotide probe are responsive to double stranded DNA and are capable of producing a detectable fluorescence being upon activation during the step of amplifying in response to double stranded DNA production during amplifying.

In certain example embodiments, the fluorophore of at least one of the first oligonucleotide probes is different from the fluorophore of the second oligonucleotide probe.

In certain example embodiments, detection occurs during the step of amplifying.

In certain example embodiments, amplifying further comprises contacting the amplified double stranded DNA fragment of the ATP-ADP carrier protein gene, the EHP spore gene, or both, and optionally the amplified double stranded DNA fragment of the EHP spore wall gene with a detectable dye molecule that binds double stranded DNA and optionally contacting the amplified double stranded DNA fragment of the control gene with a detectable dye molecule that binds double stranded DNA.

In certain example embodiments, contacting the amplified double stranded DNA fragment of the ATP-ADP carrier protein gene, the EHP spore gene, or the EHP spore wall gene with a detectable dye molecule that binds double stranded DNA occurs during the step of amplifying.

In certain example embodiments, amplifying the ATP-ADP carrier protein gene, the EHP spore gene, or both, and optionally amplifying the EHP spore wall gene and amplifying the control gene is carried out in the same PCR reaction.

In certain example embodiments, amplifying the ATP-ADP carrier protein gene, the EHP spore gene, or both, and optionally amplifying the EHP spore wall gene and the amplifying the control gene is carried out in the different PCR reactions.

In certain example embodiments, the first oligonucleotide primer of at least one of the one or more first primer pairs has a sequence according to SEQ ID NO: 4, the second oligonucleotide primer of at least one of the one or more second primer pairs has a sequence according to SEQ ID NO: 5; or both.

In certain example embodiments, there is no detectable non-specific amplification of a PCR product.

In certain example embodiments, the assay does not detect a non-EHP organism selected from the group consisting of: *Enterocytospora artemiae*, acute hepatopancreatic necrosis disease (AHPND), infectious hypodermal and hematopoietic necrosis virus (IHHNV), necrotizing hepatopancreatitis (NHP), white spot syndrome virus (WSSV), infectious myonecrosis virus (IMNV), *Penaeus vannamei* nodavirus (PvNV), Taura syndrome virus (TSV), yellowhead disease (YHV), and combinations thereof.

The PCR method employed in the assay herein can be any suitable PCR method. PCR methods include, but are not limited to, such as PCR, RT-PCR, nested-PCR, real-time PCR methods, multiplexed PRC, long-range PCR, single cell PCR, fast-cycling PCR, Methylation specific PCR, hot-start PCR, Hi-fidelity PCR, asymmetric PCR, overlap extension PCR, ligation mediated PCR, solid-phase PCR, touch down PCR, The PCR can be designed to amplify genomic DNA or be adapted to detect expression of a gene, such as RT-PCR. In some embodiments, the PCR method is qualitative. In some embodiments, the PCR method is quantitative. The PCR can be performed using any suitable machines, which are commercially available. Methods of interpreting results, qualitatively or quantitatively, are generally known in the art. See e.g. M. W. Pfaffl. "Relative quantification" pgs. 63-82 in Real-Time PCR ed. T. Dorak. Published by International University and Fronhoffs et al. 2002. Mol. Cell. Probes 16:99-110. In some embodiments, the PCR method includes generation of a standard curve (e.g. a standard cRNA or cDNA curve) such that molecules of amplicons produced from a sample can be quantified.

The PCR reaction can be carried out in any suitable reaction volume. In some embodiments, the reaction volume can range from or be 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16, 16.1, 16.2, 16.3, 16.4, 16.5, 16.6, 16.7, 16.8, 16.9, 17, 17.1, 17.2, 17.3, 17.4, 17.5, 17.6, 17.7, 17.8, 17.9, 18, 18.1, 18.2, 18.3, 18.4, 18.5, 18.6, 18.7, 18.8, 18.9, 19, 19.1, 19.2, 19.3, 19.4, 19.5, 19.6, 19.7, 19.8, 19.9, 20, 20.1, 20.2, 20.3, 20.4, 20.5, 20.6, 20.7, 20.8, 20.9, 21, 21.1, 21.2, 21.3, 21.4, 21.5, 21.6, 21.7, 21.8, 21.9, 22, 22.1, 22.2, 22.3, 22.4, 22.5, 22.6, 22.7, 22.8, 22.9, 23, 23.1, 23.2, 23.3, 23.4, 23.5, 23.6, 23.7, 23.8, 23.9, 24, 24.1, 24.2, 24.3, 24.4, 24.5, 24.6, 24.7, 24.8, 24.9, 25, 25.1, 25.2, 25.3, 25.4, 25.5, 25.6, 25.7, 25.8, 25.9, 26, 26.1, 26.2, 26.3, 26.4, 26.5, 26.6, 26.7, 26.8, 26.9, 27, 27.1, 27.2, 27.3, 27.4, 27.5, 27.6, 27.7, 27.8, 27.9, 28, 28.1, 28.2, 28.3, 28.4, 28.5, 28.6, 28.7, 28.8, 28.9, 29, 29.1, 29.2, 29.3, 29.4, 29.5, 29.6, 29.7, 29.8, 29.9, 30, 30.1, 30.2, 30.3, 30.4, 30.5, 30.6, 30.7, 30.8, 30.9, 31, 31.1, 31.2, 31.3, 31.4, 31.5, 31.6, 31.7, 31.8, 31.9, 32, 32.1, 32.2, 32.3, 32.4, 32.5, 32.6, 32.7, 32.8, 32.9, 33, 33.1, 33.2, 33.3, 33.4, 33.5, 33.6, 33.7, 33.8, 33.9, 34, 34.1, 34.2, 34.3, 34.4, 34.5, 34.6, 34.7, 34.8, 34.9, 35, 35.1, 35.2, 35.3, 35.4, 35.5, 35.6, 35.7, 35.8, 35.9, 36, 36.1, 36.2, 36.3, 36.4, 36.5, 36.6, 36.7, 36.8, 36.9, 37, 37.1, 37.2, 37.3, 37.4, 37.5, 37.6, 37.7, 37.8, 37.9, 38, 38.1, 38.2, 38.3, 38.4, 38.5, 38.6, 38.7, 38.8, 38.9, 39, 39.1, 39.2, 39.3, 39.4, 39.5, 39.6, 39.7, 39.8, 39.9, 40, 40.1, 40.2, 40.3, 40.4, 40.5, 40.6, 40.7, 40.8, 40.9, 41, 41.1, 41.2, 41.3, 41.4, 41.5, 41.6, 41.7, 41.8, 41.9, 42, 42.1, 42.2, 42.3, 42.4, 42.5, 42.6, 42.7, 42.8, 42.9, 43, 43.1, 43.2, 43.3, 43.4, 43.5, 43.6, 43.7, 43.8, 43.9, 44, 44.1, 44.2, 44.3, 44.4, 44.5, 44.6, 44.7, 44.8, 44.9, 45, 45.1, 45.2, 45.3, 45.4, 45.5, 45.6, 45.7, 45.8, 45.9, 46, 46.1, 46.2, 46.3, 46.4, 46.5, 46.6, 46.7, 46.8, 46.9, 47, 47.1, 47.2, 47.3, 47.4, 47.5, 47.6, 47.7, 47.8, 47.9, 48, 48.1, 48.2, 48.3, 48.4, 48.5, 48.6, 48.7, 48.8, 48.9, 49, 49.1, 49.2, 49.3, 49.4, 49.5, 49.6, 49.7, 49.8, 49.9, 50, 50.1, 50.2, 50.3, 50.4, 50.5, 50.6, 50.7, 50.8, 50.9, 51, 51.1, 51.2, 51.3, 51.4, 51.5, 51.6, 51.7, 51.8, 51.9, 52, 52.1, 52.2, 52.3, 52.4, 52.5, 52.6, 52.7, 52.8, 52.9, 53, 53.1, 53.2, 53.3, 53.4, 53.5, 53.6, 53.7, 53.8, 53.9, 54, 54.1, 54.2, 54.3, 54.4, 54.5, 54.6, 54.7, 54.8, 54.9, 55, 55.1, 55.2, 55.3, 55.4, 55.5, 55.6, 55.7, 55.8, 55.9, 56, 56.1, 56.2, 56.3, 56.4, 56.5, 56.6, 56.7, 56.8, 56.9, 57, 57.1, 57.2, 57.3, 57.4, 57.5, 57.6, 57.7, 57.8, 57.9, 58, 58.1, 58.2, 58.3, 58.4, 58.5, 58.6, 58.7, 58.8, 58.9, 59, 59.1, 59.2, 59.3, 59.4, 59.5, 59.6, 59.7, 59.8, 59.9, 60, 60.1, 60.2, 60.3, 60.4, 60.5, 60.6, 60.7, 60.8, 60.9, 61, 61.1, 61.2, 61.3, 61.4, 61.5, 61.6, 61.7, 61.8, 61.9, 62, 62.1, 62.2, 62.3, 62.4, 62.5, 62.6, 62.7, 62.8, 62.9, 63, 63.1, 63.2, 63.3, 63.4, 63.5, 63.6, 63.7, 63.8, 63.9, 64, 64.1, 64.2, 64.3, 64.4, 64.5, 64.6, 64.7, 64.8, 64.9, 65, 65.1, 65.2, 65.3, 65.4, 65.5, 65.6, 65.7, 65.8, 65.9, 66, 66.1, 66.2, 66.3, 66.4, 66.5, 66.6, 66.7, 66.8, 66.9, 67, 67.1, 67.2, 67.3, 67.4, 67.5, 67.6, 67.7, 67.8, 67.9, 68, 68.1, 68.2, 68.3, 68.4, 68.5, 68.6, 68.7, 68.8, 68.9, 69, 69.1, 69.2, 69.3, 69.4, 69.5, 69.6, 69.7, 69.8, 69.9, 70, 70.1, 70.2, 70.3, 70.4, 70.5, 70.6, 70.7, 70.8, 70.9, 71, 71.1, 71.2, 71.3, 71.4, 71.5, 71.6, 71.7, 71.8, 71.9, 72, 72.1, 72.2, 72.3, 72.4, 72.5, 72.6, 72.7, 72.8, 72.9, 73, 73.1, 73.2, 73.3, 73.4, 73.5, 73.6, 73.7, 73.8, 73.9, 74, 74.1, 74.2, 74.3, 74.4, 74.5, 74.6, 74.7, 74.8, 74.9, 75, 75.1, 75.2, 75.3, 75.4, 75.5, 75.6, 75.7, 75.8, 75.9, 76, 76.1, 76.2, 76.3, 76.4, 76.5, 76.6, 76.7, 76.8, 76.9, 77, 77.1, 77.2, 77.3, 77.4, 77.5, 77.6, 77.7, 77.8, 77.9, 78, 78.1, 78.2, 78.3, 78.4, 78.5, 78.6, 78.7, 78.8, 78.9, 79, 79.1, 79.2, 79.3, 79.4, 79.5, 79.6, 79.7, 79.8, 79.9, 80, 80.1, 80.2, 80.3, 80.4, 80.5, 80.6, 80.7, 80.8, 80.9, 81, 81.1, 81.2, 81.3, 81.4, 81.5, 81.6, 81.7, 81.8, 81.9, 82, 82.1, 82.2, 82.3, 82.4, 82.5, 82.6, 82.7, 82.8, 82.9, 83, 83.1, 83.2, 83.3, 83.4, 83.5, 83.6, 83.7, 83.8, 83.9, 84, 84.1, 84.2, 84.3, 84.4, 84.5, 84.6, 84.7, 84.8, 84.9, 85, 85.1, 85.2, 85.3, 85.4, 85.5, 85.6, 85.7, 85.8, 85.9, 86, 86.1, 86.2, 86.3, 86.4, 86.5, 86.6, 86.7, 86.8, 86.9, 87, 87.1, 87.2, 87.3, 87.4, 87.5, 87.6, 87.7, 87.8, 87.9, 88, 88.1, 88.2, 88.3, 88.4, 88.5, 88.6, 88.7, 88.8, 88.9, 89, 89.1, 89.2, 89.3, 89.4, 89.5, 89.6, 89.7, 89.8, 89.9, 90, 90.1, 90.2, 90.3, 90.4, 90.5, 90.6, 90.7, 90.8, 90.9, 91, 91.1, 91.2, 91.3, 91.4, 91.5, 91.6, 91.7, 91.8, 91.9, 92, 92.1, 92.2, 92.3, 92.4, 92.5, 92.6, 92.7, 92.8, 92.9, 93, 93.1, 93.2, 93.3, 93.4, 93.5, 93.6, 93.7, 93.8, 93.9, 94, 94.1, 94.2, 94.3, 94.4, 94.5, 94.6, 94.7, 94.8, 94.9, 95, 95.1, 95.2, 95.3, 95.4, 95.5, 95.6, 95.7, 95.8, 95.9, 96, 96.1, 96.2, 96.3, 96.4, 96.5, 96.6, 96.7, 96.8, 96.9, 97, 97.1, 97.2, 97.3, 97.4, 97.5, 97.6, 97.7, 97.8, 97.9, 98, 98.1, 98.2, 98.3, 98.4, 98.5, 98.6, 98.7, 98.8, 98.9, 99, 99.1, 99.2, 99.3, 99.4, 99.5, 99.6, 99.7, 99.8, 99.9, to/or 100 pL, nL, microliter, mL or more. The PCR reaction can be carried out in any suitable reaction vessel, microfluidic vessel, or on any suitable substrate that is capable of maintaining segregated, addressable droplets.

In some embodiments, such as those employing real-time PCR methods of gene fragment amplification, an oligonucleotide probe specific to the target polynucleotide (e.g. gene or transcript) and primer set can be used. An example of such a probe is a TaqMan® probe. Different genes can be detected in the same reaction using TaqMan® probes by using a different fluorophore on each probe so that the gene amplification from each gene can be differentiated based on the fluorescence produced. Quencher molecules can be fluorescent (e.g., TAMRA™) or nonfluorescent molecules e.g. DABCYL and Black Hole Quencher®). Example fluorophores include, but are not limited to 6-FAM™, JOE™, TET™, Cal Fluor® Gold 540, HEX™, Cal Fluor® Orange 560, TAMRA™, VIC™, Cyanine 3, Quasar® 570, Cal Fluor® Orange 590, ROX™, Texas Red®, Cyanine 5, Quasar® 670, and Cyanine 5.5.

In some embodiments, including but not limited to those employing real-time PCR methods of gene fragment amplification, a fluorescent dye that binds to double stranded DNA can be used to monitor gene fragment amplification during each PCR reaction cycle. An example of such a dye is SYBR® Green and its variants. In some embodiments, the detectable dye molecule that binds double stranded DNA is a cyanine dye. In some embodiments, the detectable dye molecule that binds double stranded DNA is N',N'-dimethyl-N-[4-[(E)-(3-methyl-1,3-benzothiazol-2-ylidene)methyl]-1-phenylquinolin-1-ium-2-yl]-N-propylpropane-1,3-diamine and variants thereof.

In assays where multiple genes are amplified in a single reaction (also referred to in the art as a "multiplexed reaction" or simply "multiplexing") where a fluorescent dye that binds to double stranded DNA is used to monitor amplification of gene fragments, the amount (relative or quantitative) of gene fragments amplified from the different genes present in the reaction can be distinguished from each other by virtue of different melting curves. Primer sets can be designed for each gene in the multiplex reaction such that the gene fragment generated will disassociate at a different temperature and thus produce a different melting curve. This can allow for multiplexing in reactions where amplicon specific probes are not employed.

In some embodiments, the PCR-based assays (single or multiplexed reactions) described herein that can be capable of specifically detecting EHP infection in a shrimp or population thereof, shrimp feed, and/or feed ingredient can be configured to detect one or more of the following genes: an ATP-ADP carrier protein gene and/or EHP spore gene, and optionally EHP spore wall gene. In some embodiments, the assay can be capable of detecting an ATP-ADP carrier protein gene and optionally at least one other gene such as an EHP spore gene, and/or an EHP spore wall gene. In some embodiments, the only disease-specific gene that the assay detects and/or amplifies is an ATP-ADP carrier protein gene.

In some embodiments, an assay to detect EHP infection in a shrimp or population thereof, shrimp feed, and/or feed ingredient can include the steps of specifically amplifying a fragment of an ATP-ADP carrier protein gene and/or EHP spore gene, and optionally a EHP spore wall gene (e.g., GenBank Accession No. KX258197) using a polymerase chain reaction (PCR) method, wherein the step of amplifying includes contacting a nucleic acid sample obtained from one or more shrimp, shrimp feed, and/or feed ingredient with a first oligonucleotide primer pair having a first oligonucleotide primer and a second oligonucleotide primer, wherein the first oligonucleotide primer is a forward direction oligonucleotide primer adapted for specific PCR amplification of a fragment of an ATP-ADP carrier protein gene, an EHP spore gene, or both, and EHP spore wall gene with the second oligonucleotide primer and specifically binds a region of the ATP-ADP carrier protein gene, the EHP spore gene, or the EHP spore wall gene, wherein the second oligonucleotide primer is a reverse direction oligonucleotide primer adapted for PCR amplification of a fragment of the ATP-ADP carrier protein gene, the EHP spore gene, or the optional EHP spore wall gene, with the first oligonucleotide primer and specifically binds a region of the ATP-ADP carrier protein gene, the EHP spore gene, or the optional EHP spore wall gene; and the step of detecting the presence or absence of an amplified double stranded DNA fragment of the ATP-ADP carrier protein gene, the EHP spore gene, or both, and the optional EHP spore wall gene, in the nucleic acid sample. In some embodiments, the step of detection can occur during the step of amplifying. In other words, the fragment is amplified and detected in real-time as each amplification cycle occurs. This is also referred to in the art as real-time PCR.

The step of amplifying can further include contacting the nucleic acid sample with a first oligonucleotide probe adapted for real-time PCR amplification and detection, wherein the first oligonucleotide probe specifically binds a region of an ATP-ADP carrier protein gene, an EHP spore gene, or optionally the EHP spore wall gene that is between the region of the ATP-ADP carrier protein gene, the EHP spore gene, or the EHP spore wall gene where the first oligonucleotide primer specifically binds and the region of the ATP-ADP carrier protein gene, the EHP spore gene, or the EHP spore wall gene where the second oligonucleotide primer specifically binds, and wherein the first oligonucleotide probe is coupled to a fluorophore and a quencher molecule. The fluorophore of the first oligonucleotide probe is released during the step of amplifying and produces detectable fluorescence.

The step of amplifying can further include contacting the nucleic acid sample with a third oligonucleotide primer and a fourth oligonucleotide primer, wherein the third oligonucleotide primer is a forward direction oligonucleotide primer adapted for PCR amplification of a fragment of a control (e.g. housekeeping gene) with the fourth oligonucleotide primer and specifically binds a region of the control gene, wherein the fourth oligonucleotide primer is a reverse direction oligonucleotide primer adapted for PCR amplification of a fragment of the control gene with the third oligonucleotide primer and specifically binds a region of the control gene, and wherein the step of detecting further includes detecting the presence or absence of an amplified double stranded DNA fragment of the control gene. Suitable control genes include the beta actin gene or the 18S rRNA gene of shrimp.

In some embodiments, the step of amplifying the ATP-ADP carrier protein gene fragment and/or the EHP spore gene fragment, and the optional the EHP spore wall gene fragment and the step of amplifying the control gene fragment can be carried out in the same PCR reaction. In some embodiments, the step of amplifying the ATP-ADP carrier protein gene fragment and/or EHP spore gene fragment, and optionally the EHP spore wall gene fragment and the step of amplifying the control gene fragment carried out in the different PCR reactions.

The step of amplifying can further include contacting the nucleic acid sample with a second oligonucleotide probe adapted for real-time PCR amplification and detection, wherein the second oligonucleotide probe specifically binds a region of the control gene that is between the region of the control gene of shrimp where the third oligonucleotide primer specifically binds and the region of the control gene where the fourth oligonucleotide primer specifically binds, and wherein the second oligonucleotide probe is coupled to a fluorophore and a quencher molecule. The fluorophore of the second oligonucleotide probe can be released during the step of amplifying and produces detectable fluorescence. The fluorophore of the second oligonucleotide probe can be different from the fluorophore of the first oligonucleotide probe.

The step of amplifying can further include contacting the amplified double stranded DNA fragment of the ATP-ADP carrier protein gene fragment, the optional EHP spore gene fragment, or the EHP spore wall gene fragment, control gene, or any combination thereof with a detectable dye molecule that binds double stranded DNA. The step of contacting the amplified double stranded DNA fragment of the ATP-ADP carrier protein gene fragment, the EHP spore gene fragment, or the optional EHP spore wall gene fragment, control gene, or any combination thereof with a detectable dye molecule that binds double stranded DNA can occur during the step of amplifying. In these embodiments, as the fragments are produced during each PCR cycle, the detectable dye molecule(s) are associated or otherwise integrated with the double stranded DNA fragments being produced.

It will be appreciated that the step of amplifying can contain at least two or more cycles where the number of amplicons is approximately doubled each cycle. The exact steps within each cycle will vary depending on the PCR technique used, but all include separating or partially separating a double stranded DNA molecule to create single stranded DNA molecules contacting the resulting template single stranded DNA molecule(s) with one or more primers and a DNA polymerase, and allowing the polymerase to incorporate free nucleotides into a new strand that is an extension of the primer that is bound to the template DNA molecule, thus forming a new double stranded DNA molecule. This is repeated for a desired number of cycles to generate a pool of amplicons. In some embodiments, the number of cycles can range from about 2 to about 70, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70. In some embodiments, the number of cycles performed is 28, 29, 30, 31, 32, 33, 34, 35, 36, 37, 38, 39, 40, 41, 42, or 43. In some embodiments, the PCR method can include an initial denaturation step or other steps before the amplification cycles begin. In some embodiments, the PCR method can include other steps and processes after the final amplification cycle occurs, such as a final extension step or melting curve analysis. In some embodiments, a melting curve analysis can be performed as amplification is occurring at each cycle.

In some embodiments, the first oligonucleotide primer has a sequence according to SEQ ID NO: 4. The second oligonucleotide primer has a sequence according to SEQ ID NO: 5. In some embodiments there is no detectable or measurable non-specific amplification of a PCR product. In other words, the assay does not detect or produce non-specific amplification of PCR product. In some embodiments, the assay does not detect a non-EHP organism selected from the group consisting of: *Enterocytospora artemiae*, acute hepatopancreatic necrosis disease (AHPND), infectious hypodermal and hematopoietic necrosis virus (IHHNV), necrotizing hepatopancreatitis (NHP), white spot syndrome virus (WSSV), infectious myonecrosis virus (IMNV), *Penaeus vannamei* nodavirus (PvNV), Taura syndrome virus (TSV), yellowhead disease (YHV), and combinations thereof.

Kits for Specific Detection of EHP

Also described herein are kits that can be used to detect EHP in shrimp, shrimp feed, and/or feed ingredient(s). The kits can include one or more primer sets and/or probes that can be used to amplify and specifically detect the ATP-ADP carrier protein gene fragment and/or the EHP spore gene fragment, optionally the EHP spore wall gene fragment, and optionally a control gene. The kits can also contain one or more reagents need to perform a PCR-based reaction including but not limited to, nucleotides, a polymerase (e.g. a Taq polymerase), buffers, salts, preservatives, dyes, etc. In some aspects, an amount of SYBR Green or a variant thereof is provided in the Kit. the ATP-ADP carrier protein gene fragment, the EHP spore gene fragment, or the EHP spore wall gene fragment, control gene, or any combination thereof In some embodiments, the kit can include a first primer pair adapted for PCR, wherein the first primer pair comprises a first oligonucleotide primer and a second oligonucleotide primer, wherein the first oligonucleotide primer is a forward direction oligonucleotide primer adapted for PCR amplification of a fragment of the ATP-ADP carrier protein gene, and/or EHP spore gene, and optionally EHP spore wall gene with the second oligonucleotide primer and specifically binds a region of the ATP-ADP carrier protein gene, the EHP spore gene, or optionally the EHP spore wall gene, and wherein the second oligonucleotide primer is a reverse direction oligonucleotide primer adapted for PCR amplification of a fragment of the ATP-ADP carrier protein gene, the EHP spore gene, or optionally the EHP spore wall gene with the first oligonucleotide primer and specifically binds a region of the ATP-ADP carrier protein gene, the EHP spore gene, or optionally the EHP spore wall gene. In some embodiments, the kit can include an oligonucleotide primer pair capable of detecting and/or amplifying an ATP-ADP carrier protein gene and optionally at least one or more other oligonucleotide primer pair(s) capable of detecting and/or amplifying at least one gene, including but not limited to, an EHP spore gene, and/or an EHP spore wall gene. In some embodiments, the only oligonucleotide primer pair designed to amplify a disease specific gene contained in the kit is an oligonucleotide primer pair capable of detecting and/or amplifying an ATP-ADP carrier protein gene.

The kit can further include a second primer pair adapted for PCR, wherein the second primer pair comprises a third oligonucleotide primer and a fourth oligonucleotide primer, wherein the third oligonucleotide primer is a forward direction oligonucleotide primer adapted for PCR amplification of a fragment of a control gene (e.g. a beta actin gene or the 18S rRNA gene of shrimp) with the fourth oligonucleotide primer and specifically binds a region of the beta actin gene or the control gene and wherein the fourth oligonucleotide primer is a reverse direction oligonucleotide primer adapted for PCR amplification of a fragment of the control gene with the third oligonucleotide primer and specifically binds a region of the control gene.

The kit can include a first oligonucleotide probe adapted for real-time PCR, wherein the first oligonucleotide probe specifically binds a region of the ATP-ADP carrier protein gene, the EHP spore gene, or optionally the EHP spore wall gene that is between the region of the ATP-ADP carrier protein gene, the EHP spore gene, or the EHP spore wall gene where the first oligonucleotide primer specifically binds and the region of the ATP-ADP carrier protein gene, the EHP spore gene, or optionally the EHP spore wall gene where the second oligonucleotide primer specifically binds, wherein the first oligonucleotide probe is coupled to a fluorophore and a quencher molecule.

The kit can include second oligonucleotide probe, wherein the second oligonucleotide probe specifically binds a region of the control gene that is between the region of the beta actin gene or the control gene where the third oligonucleotide primer specifically binds and the region of the beta actin gene or the control gene where the fourth oligonucleotide primer specifically binds, wherein the second oligonucleotide probe is coupled to a fluorophore and a quencher molecule. The fluorophore of the first oligonucleotide probe can be different from the fluorophore of the second oligonucleotide probe.

In certain example embodiments, described herein are kits for specifically detecting *Enterocytozoon hepatopenaei* (EHP) in a nucleic acid sample via a PCR method, including one or more first primer pairs adapted for the PCR method, wherein each of the one or more first primer pairs comprises a first oligonucleotide primer and a second oligonucleotide primer, wherein each of the one or more first primer pairs are configured to specifically amplify one gene fragment from a gene selected from a shrimp ATP-ADP carrier protein gene an EHP spore gene, or both, and optionally an EHP spore wall gene, and wherein each of the one or more first primer pairs includes a first oligonucleotide primer and a second oligonucleotide primer, and wherein the each of the one or more first primer pairs are configured to specifically amplify a different gene fragment, wherein the first oligonucleotide primer of each of the one or more first primer pairs is a forward direction oligonucleotide primer adapted for PCR amplification of the one gene fragment and specifically binds the gene, and wherein the second oligonucleotide primer of each of the one or more first primer pairs is a reverse direction oligonucleotide primer adapted for PCR amplification of the one gene fragment and specifically binds the gene at a different location on the gene then the first oligonucleotide primer; and optionally further comprising a second primer pair adapted for the PCR method, wherein the second primer pair comprises a third oligonucleotide primer and a fourth oligonucleotide primer, wherein the third oligonucleotide primer is a forward direction oligonucleotide primer adapted for amplification of a fragment of a control gene with the fourth oligonucleotide primer and specifically binds a region of the control gene, and wherein the fourth oligonucleotide primer is a reverse direction oligonucleotide primer adapted for amplification of a fragment of the control gene with the third oligonucleotide primer and specifically binds a region of the control gene that is different that the region of the control gene that the third oligonucleotide primer specifically binds.

In certain example embodiments, the kit further includes an amount of a) a detectable dye molecule that binds double stranded DNA;

b) one or more first oligonucleotide probes adapted for real-time PCR, wherein each first oligonucleotide probe is configured to bind a different gene fragment selected from an ATP-ADP carrier protein gene fragment or a EHP spore gene fragment, and optionally an EHP spore wall gene, wherein each of the one or more first oligonucleotide probes specifically binds a region of the gene DNA fragment that is between a binding region of the first oligonucleotide primer and a binding region of the second oligonucleotide primer in the gene, and wherein the first oligonucleotide probe is coupled to a fluorophore and a quencher molecule;

c) a second oligonucleotide probe adapted for real-time PCR wherein the second oligonucleotide probe specifically binds a region of the control gene that is between a binding region of the third oligonucleotide primer and a binding region the fourth oligonucleotide primer, and wherein the second oligonucleotide probe is coupled to a fluorophore and a quencher molecule; or d) a combination thereof.

In certain example embodiments, the fluorophore of at least one of the first oligonucleotide probes is different from the fluorophore of at least one of the second oligonucleotide probes.

In certain example embodiments, the first oligonucleotide primer of at least one of the one or more first primer pairs has a sequence according to SEQ ID NO: 4, the second oligonucleotide primer of at least one of the one or more second primer pairs has a sequence according to SEQ ID NO: 5; or both.

The kit can further include an amount of a detectable dye molecule that binds double stranded DNA. The detectable dye molecule that binds double stranded DNA is a cyanine dye. The detectable dye molecule that binds double stranded DNA is N',N'-dimethyl-N-[4-[(E)-(3-methyl-1,3-benzothiazol-2-ylidene)methyl]-1-phenylquinolin-1-ium-2-yl]-N-propylpropane-1,3-diamine and variants thereof.

Further embodiments are illustrated in the following Examples which are given for illustrative purposes only and are not intended to limit the scope of the invention.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

The EHP (*Enterocytozoon hepatopenaei*) is a microsporidian which infect shrimp. EHP is the causative agent of hepatopancreatic microsporidiosis (HPM). The EHP infection causes growth retardation of the infected shrimp which causes economic loss to shrimp farmers. EHP infection was first detected in *Penaeus monodon* in Thailand. Subsequently EHP has been detected in *Penaeus vanamei*. EHP has been detected in several other countries including China, Indonesia, Vietnam, India and Venezualea. EHP is a critical disease in south-east Asian shrimp cultivation (Thitamadee et al 2016). The early detection of EHP is crucial to stop spread of the disease.

Different EHP detection methods have been developed. One of the detection methods is based on small subunit ribosomal RNA (SSU rRNA) gene of EHP (Tang et al. 2015. J. Invertebr. Pathol. September; 130:37-41. doi: 10.1016/j.jip.2015.06.009.). This method produces non-specific reaction with frozen Artemia. Another detection method is based on spore wall protein gene (SWP) (GenBank Accession No. KX258197) of EHP via nested-PCR (Jaroenlak et al. 2016. PLoS One. 11(11)e0166320). The nested PCR method requires running of two PCR and subsequent gel run. This method has an increased error rate.

This Example demonstrates an EHP detection method and assay based on ADP-ATP carrier protein 4 gene of EHP (GenBank: MNPJ01000024.1). The gene sequence (MNPJ01000024.1:c36086-34284 *Enterocytozoon hepatopenaei* strain TH1 scaffold_00021, whole genome shotgun sequence) was used to design PCR primers via primer3 software (www.primer3.org) program. The two primers (forward and reverse primer) were designed to produce a PCR product of 914 bp (SEQ ID NO: 6). The forward primer starts at position 351 of SEQ ID NO: 7 and the primer sequence is ATTTGACGATCCTGGTTTGG (SEQ ID NO: 4). The reverse primer starts at position 1264 of SEQ ID NO: 7 and the primer sequence is TGGCCATCGATGTGATTATG (SEQ ID NO: 5).

The details of the primers are given in Table 1 using 1-based sequence positions.

TABLE 1

| Oligo | Sequence | Start bp | length | tm | GC % | Any | 3' seq |
|---|---|---|---|---|---|---|---|
| Forward Primer | ATTTGACGATCCTGGTTTGG (SEQ ID NO: 4) | 351 | 20 | 59.79 | 45.00 | 4.0 | 1.0 |
| Reverse Primer | TGGCCATCGATGTGATTATG (SEQ ID NO: 5) | 1264 | 20 | 60.31 | 45.00 | 8.00 | 1.0 |

Sequence Size: 1803 (SEQ ID NO: 7)
Included Region Size: 1803 (SEQ ID NO: 7)

Materials and Methods:

The PCR forward and reverse primers were synthesized by IDT (www.idtdna.com) and dissolved in sterile water in 10 µM concentration mixture of forward and reverse primers.

DNA was extracted using Promega Maxwell® RSC Cell DNA Purification Kit or Qiagen Blood and tissue kit from different samples of feeds, frozen Artemia and shrimp samples. RNA was extracted from different tissues using Promega Maxwell® RSC simplyRNA Purification Kit or Qiagen RNeasy mini kit.

PCR reaction was carried out using GE Healthcare Illustra™ PuReTaq™ Ready-To-Go PCR Beads (RTG beads Catalogue #27-9558-01) using 23 µl water, 1 µl forward and reverse primer mix and 1 µl DNA of the test sample. The PCR was run on BioRad Thermocycler (T100) with following parameters: 95° C. for 5 minutes of first step, second step consisting of 35 cycles each of 95° C., 60° C., 72° C. for 30 seconds, 30 seconds and 45 seconds, respectively and a final extension of 5 minutes at 72° C. The PCR product was run on 1.5% agarose gel with 0.5×TBE buffer containing gel red dye for 1 hour and gel picture taken with BioRad Gel Doc XR+.

Results

Figure 4A:
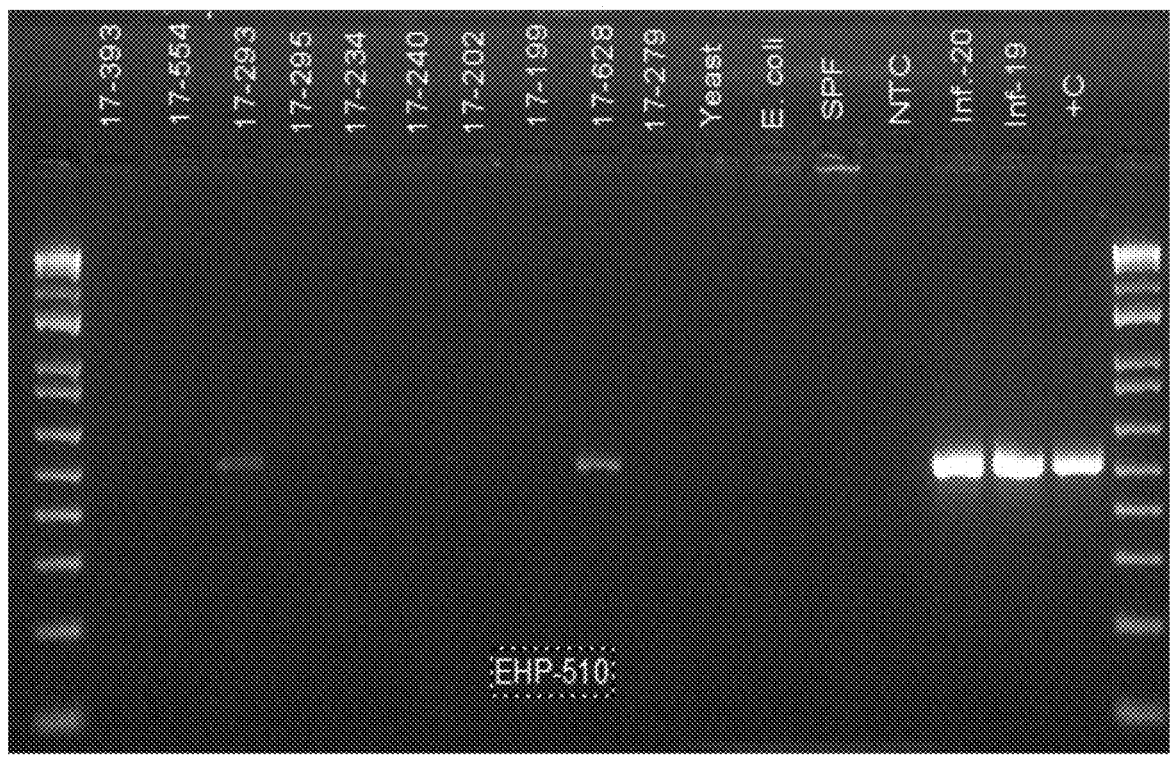
FIGS. 4A-4B—Gel images of PCR results using primer sets designed to amplify a region of the ADP-ATP carrier protein gene.
Figure 4B:
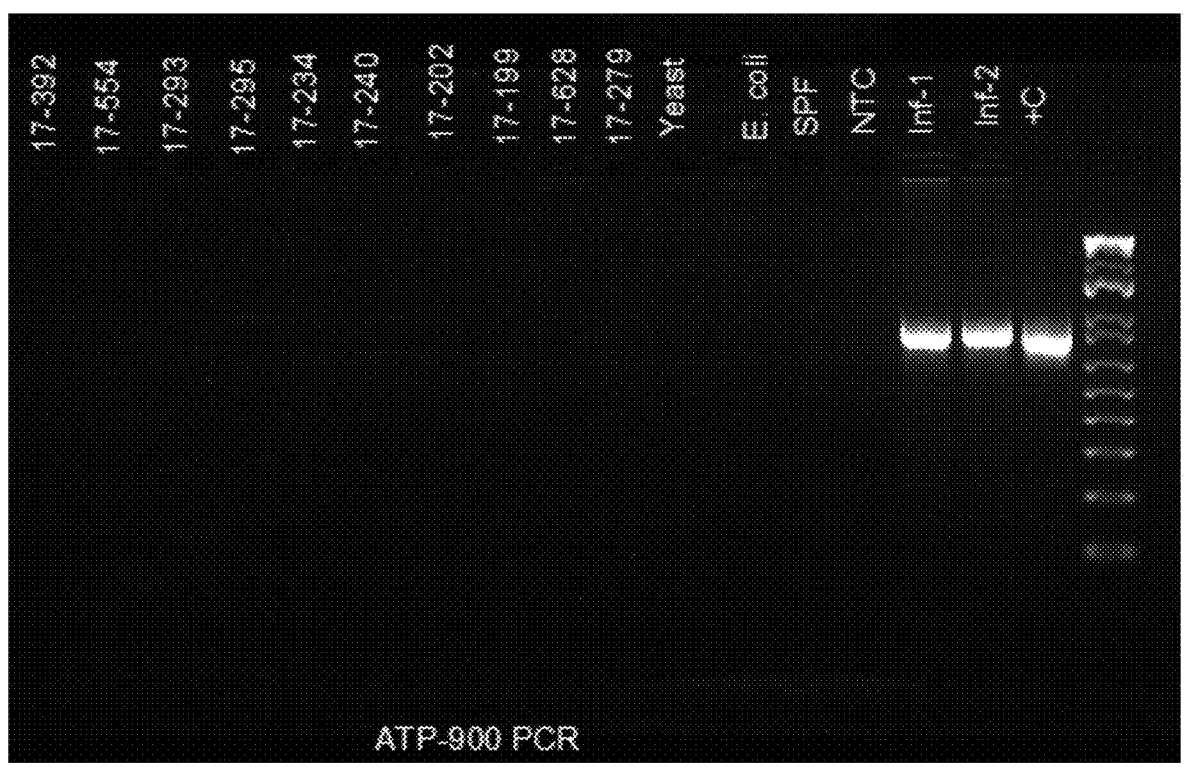

The PCR was run with EHP510 SSU rRNA primers according to the PCR conditions of Tang et al 2015. The two frozen Artemia (17-293, 17-628) produced non-specific PCR products (FIG. 4A). All the above samples were run using forward and reverse primers developed in this study, did not produce any non-specific product against above two frozen Artemia (17-293, 17-628) samples (FIG. 4B). The PCR method developed in this study detected EHP-infected samples like EHP-510 PCR (Inf-20 and Inf-19 in FIG. 4A and Inf-1 and Inf-2 in (FIG. 4B). The PCR method did not produce any product in disease free shrimp (SPF) or in non-template control (NTC), therefore this PCR detection method is specific to EHP disease detection.

Figure 5:
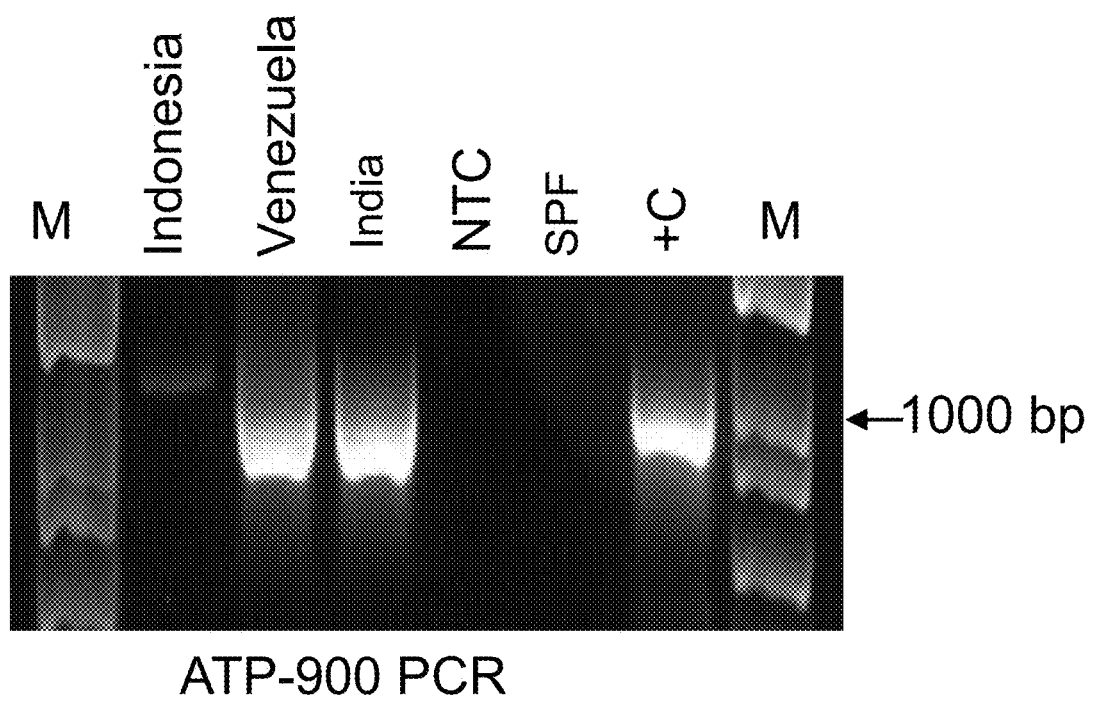
FIG. 5—Gel image of PCR results for detecting of EHP strains from different countries. M—Invitrogen 1 kb DNA ladder, Indoneasia, Venezuela, India, NTC—Non template control, SPF—Specific pathogen free, +C—Positive control.

The PCR method developed in study clearly detect shrimp-EHP disease samples from different countries such as Indonesia, Venezuela, India (FIG. 5.).

Example 2

Figure 2:
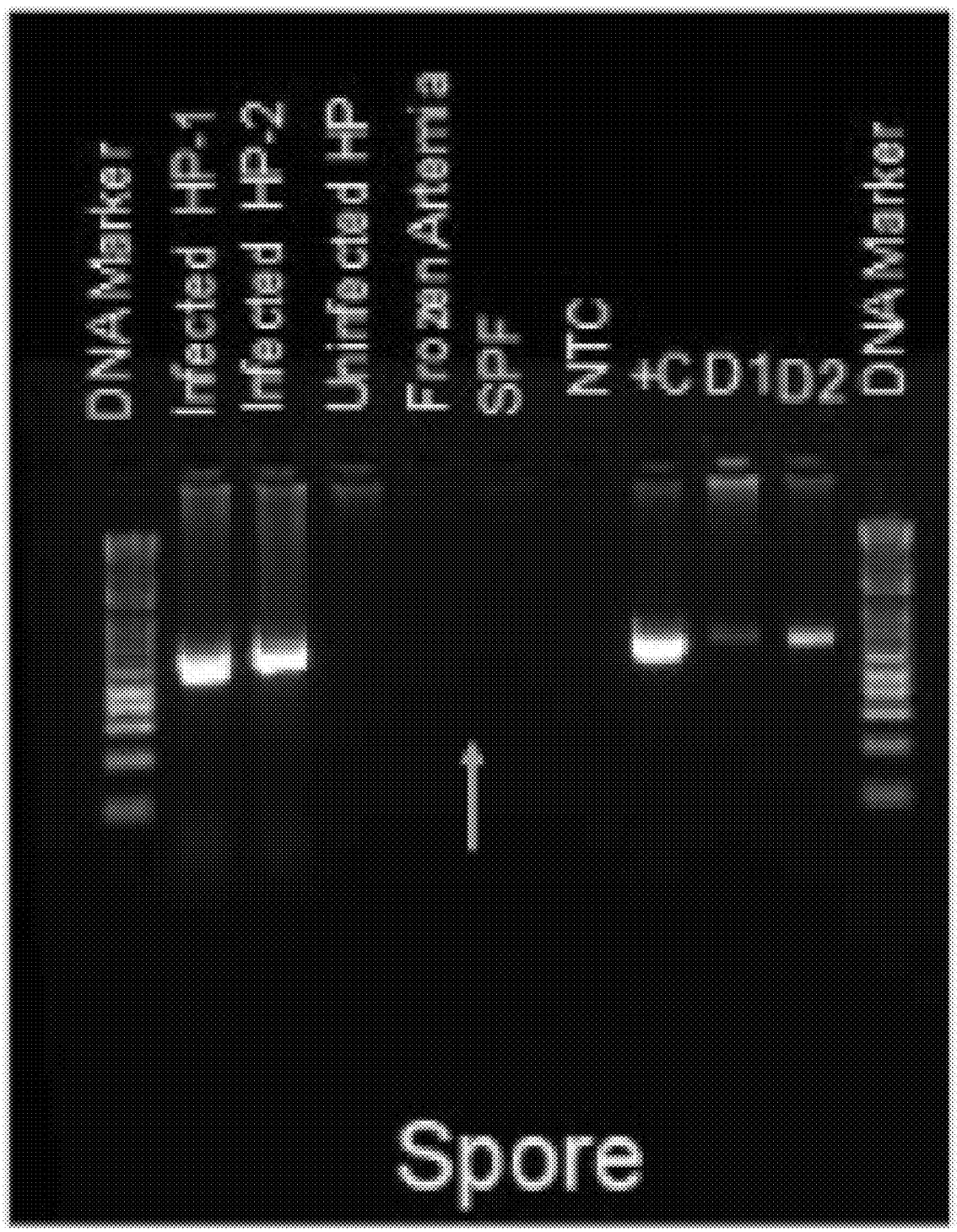
FIG. 2—Image of a gel demonstrating detection of EHP via PCR using primers designed to target and amplify spore proteins. The results can demonstrate the amplification of a specific amplicon in EHP-infected samples only. There was no observed or detectable non-specific amplicon produced in frozen Artemia samples, which were known to be EHP-negative.

FIG. 2 shows an image of gel demonstrating detection of EHP via PCR using primers designed to target and amplify spore proteins. The results can demonstrate the amplification of a specific amplicon in EHP-infected samples only. There was no observed or detectable non-specific amplicon produced in frozen Artemia samples, which were known to be EHP-negative.

Figure 3A:
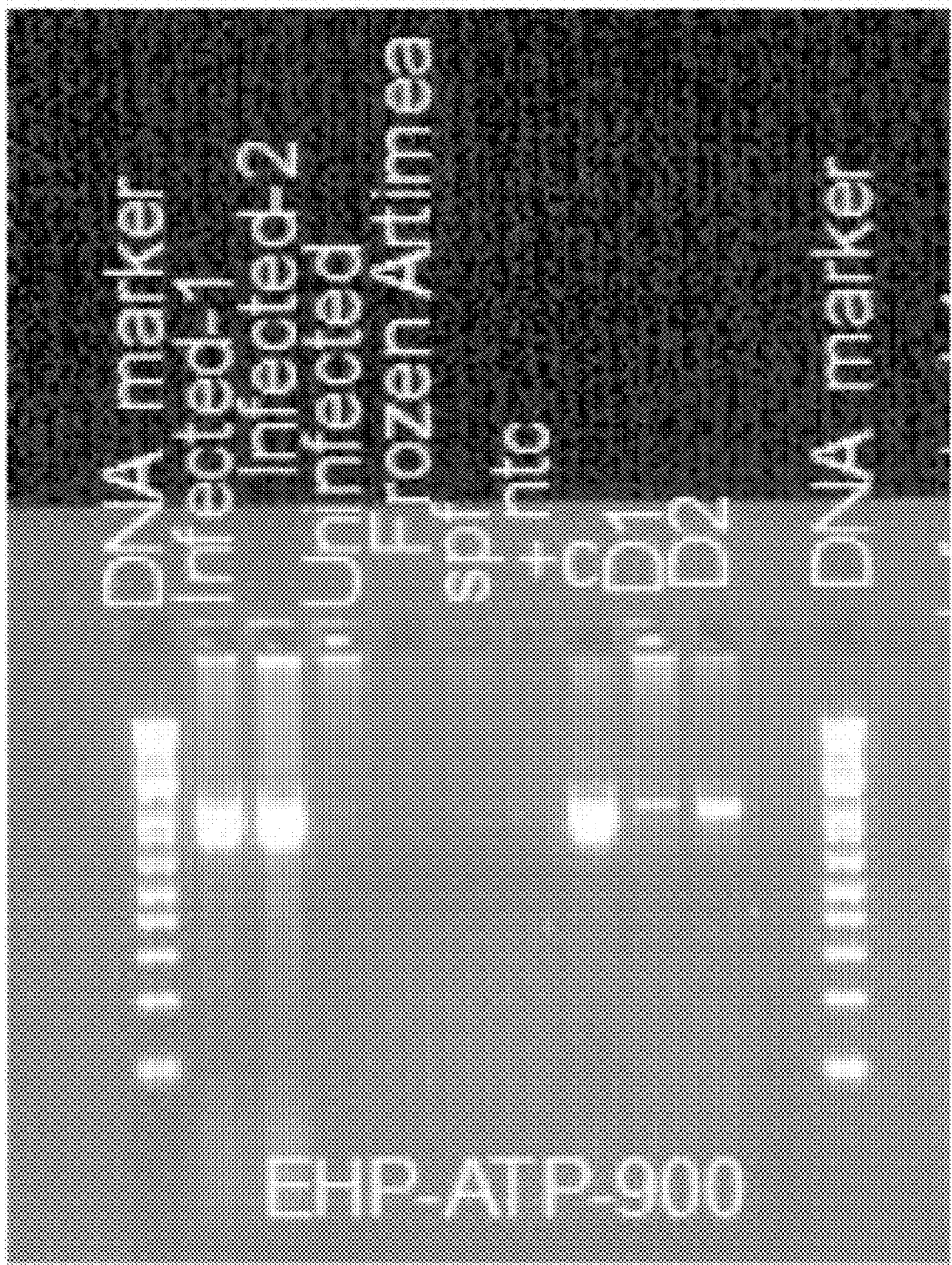
FIGS. 3A-3B—Images of gels demonstrating results of detection of EHP via PCR using primer sets designed to target and amplify a region of an ATP-transporter gene.
Figure 3B:
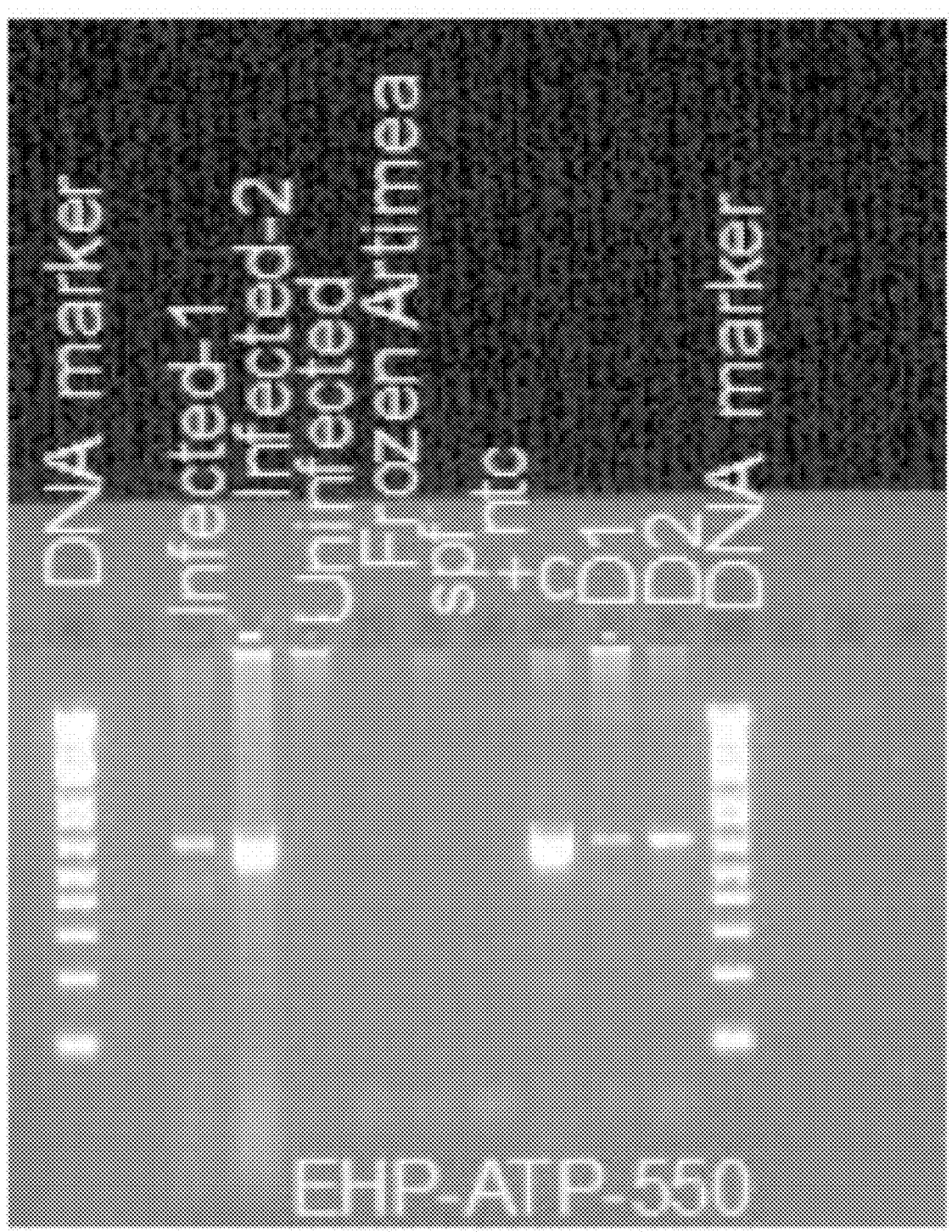

FIGS. 3A-3B show images of gels demonstrating results of detection of EHP via PCR using primer sets designed to target and amplify a region of an ATP-transporter gene. FIG. 3A and FIG. 3B can demonstrate specific amplification of EHP from infected samples without detectable non-specific amplification (as observed by no detectable detection in EHP-negative samples (frozen Artemia)).

Example 3

Figure 6A:
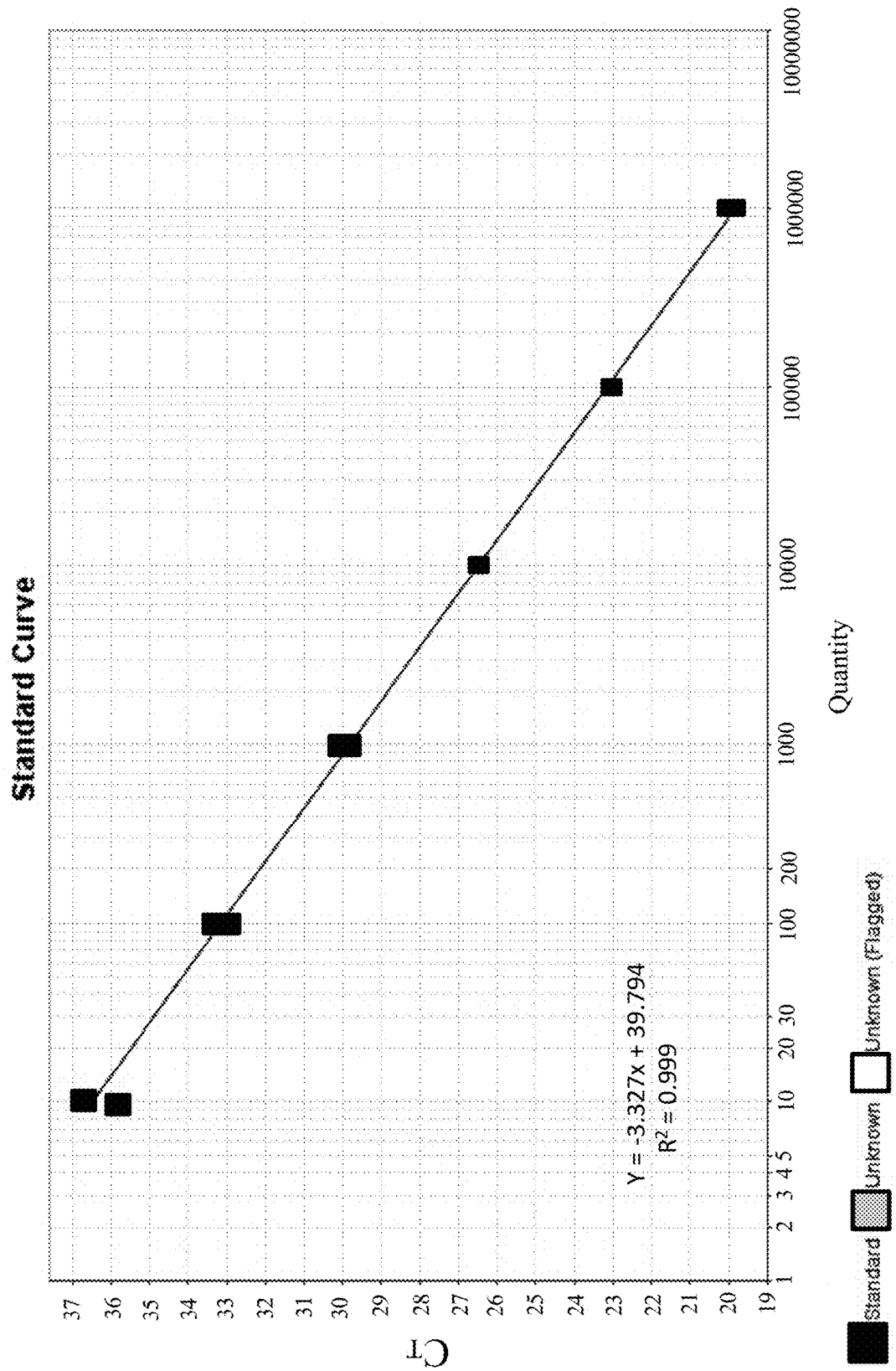
FIGS. 6A-6C—Detection of EHP by qPCR targeting the atp9000 gene.
Figure 6B:
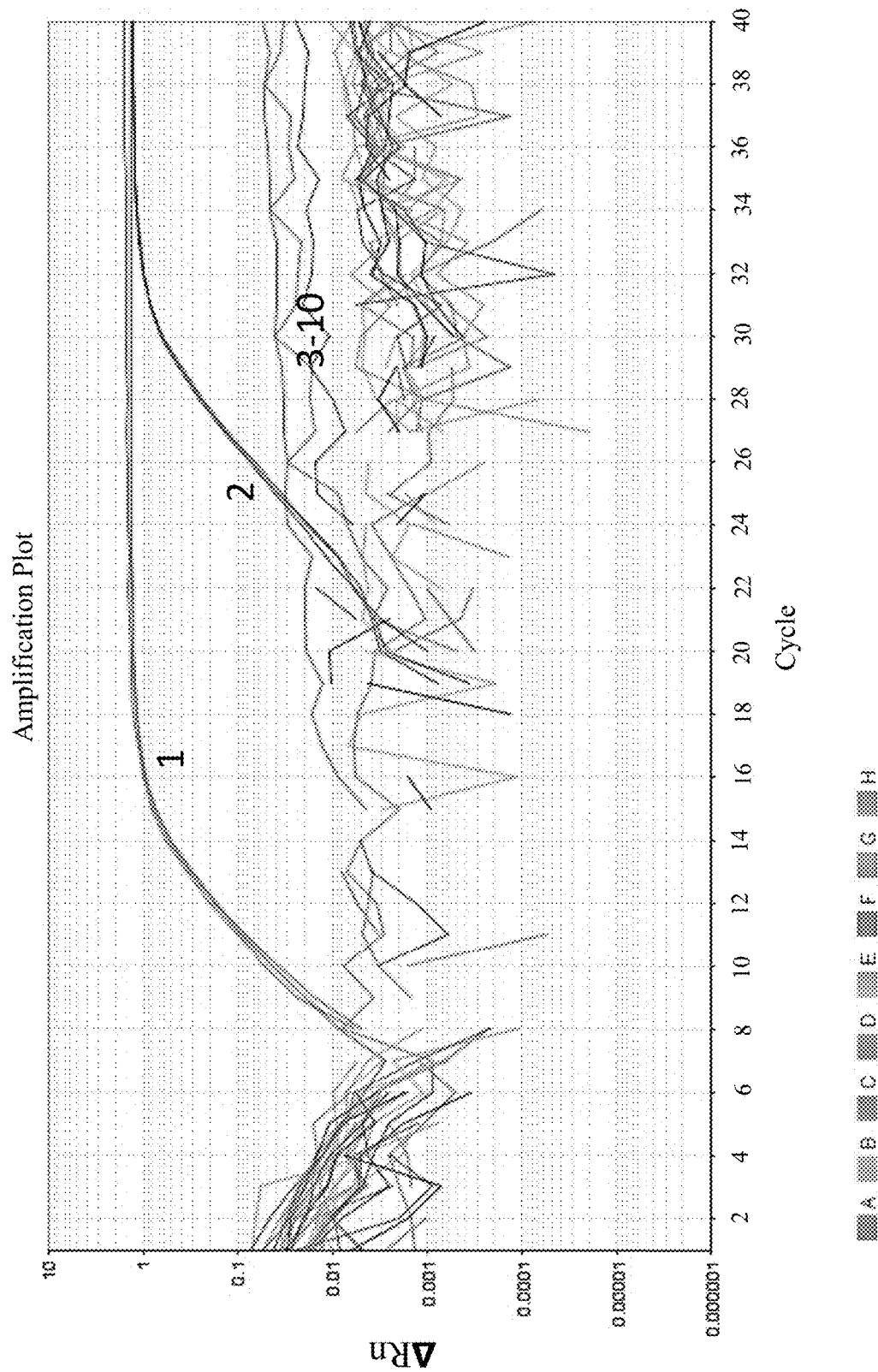
Figure 6C:
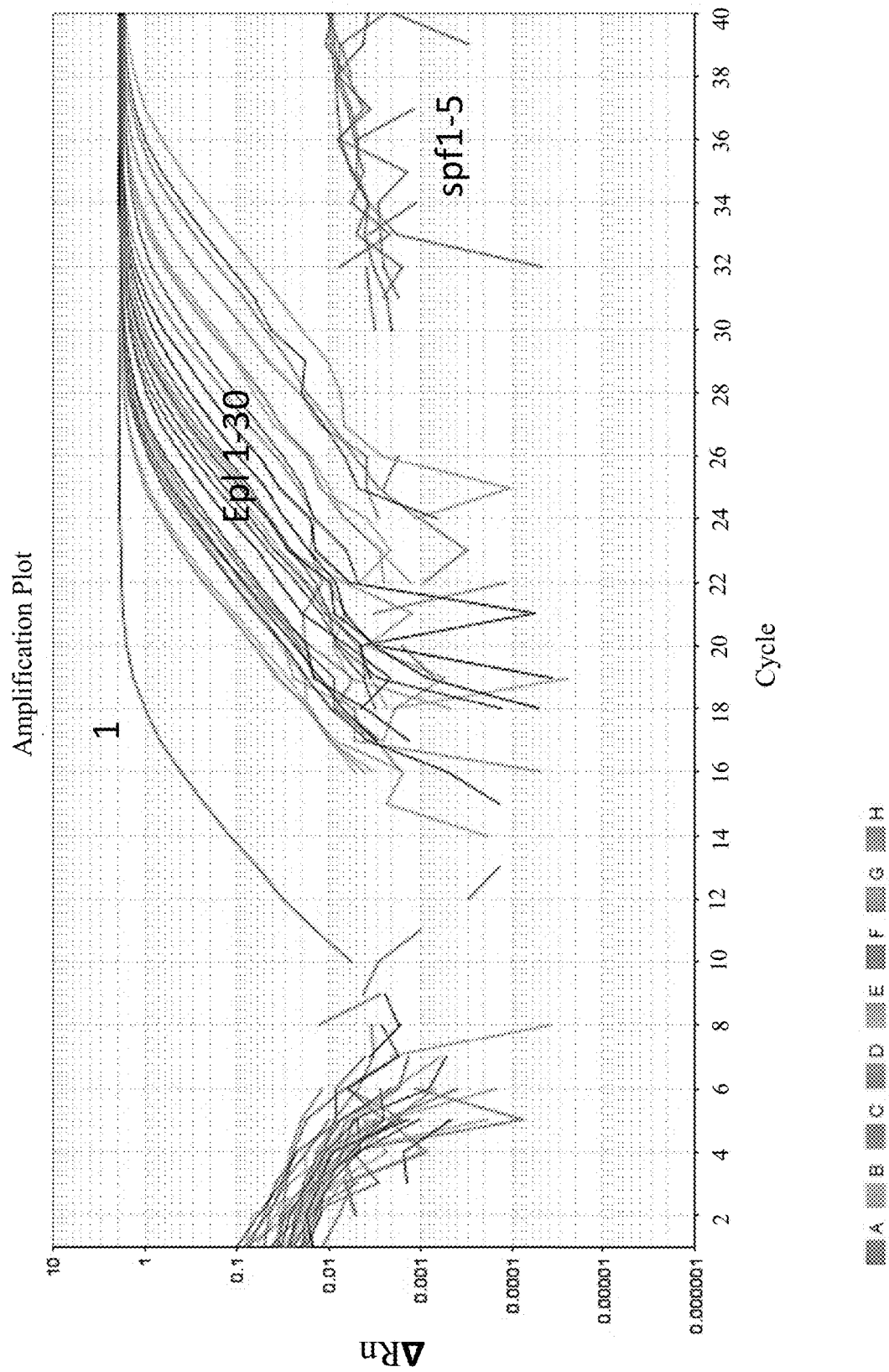

FIGS. 6A-6C can demonstrate detection of EHP by qPCR targeting the atp9000 gene. FIG. 6A shows a graph that can demonstrate a representative qPCR standard curve. FIG. 6B shows a graph that can demonstrate results from a qPCR assay capable of detecting common shrimp diseases. 1: plasmid DNA, 2: EHP-infected tissue, 3-10: (AHPND), infectious hypodermal and hematopoietic necrosis virus (IHHNV), necrotizing hepatopancreatitis (NHP), white spot syndrome virus (WSSV), infectious myonecrosis virus (IMNV), *Penaeus vannamei* nodavirus (PvNV), Taura syndrome virus (TSV), yellowhead disease (YHV), specific pathogen free (SPF), non-template control NTC). FIG. 6C shows a graph that can demonstrate screening of putative EHP-infected *P. vannamei* post-larvae. 1: plasmid DNA, Epl-1-30—EHP-infected shrimp, Specific Pathogen Free (SPF) shrimp.

Figure 7A:
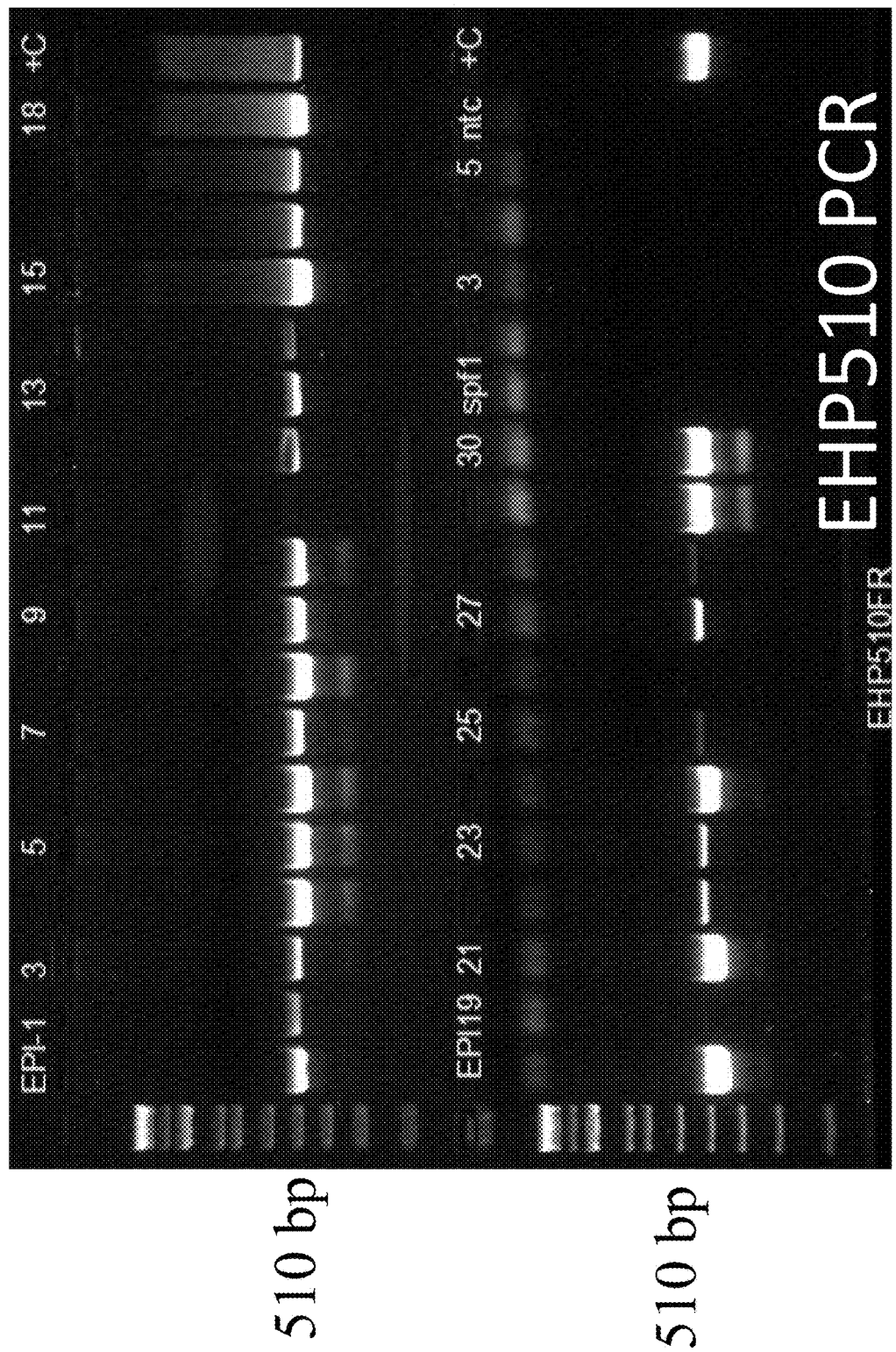
FIGS. 7A-7C—Images of representative gels that can demonstrate screening of Penaeus vannamei post-larvae for EHP by conventional PCR using primers based on ribosomal DNA small subunit (EHP510) and ATPase transporter gene (atp900). Screening of shrimp (P. vannamei) post larvae was done for infection of EHP with EHP510 primers in (FIG. 7A), atp900 primers in (FIG. 7B), and Actin in (FIG. 7C). M—Invitrogen 1 kb DNA ladder, Epl-1-30—EHP-infected independent post larvae, spf1-5 or SPF1-5—Specific pathogen free shrimp, ntc or NTC—Non-template control, +C—respective positive plasmid control.
Figure 7B:
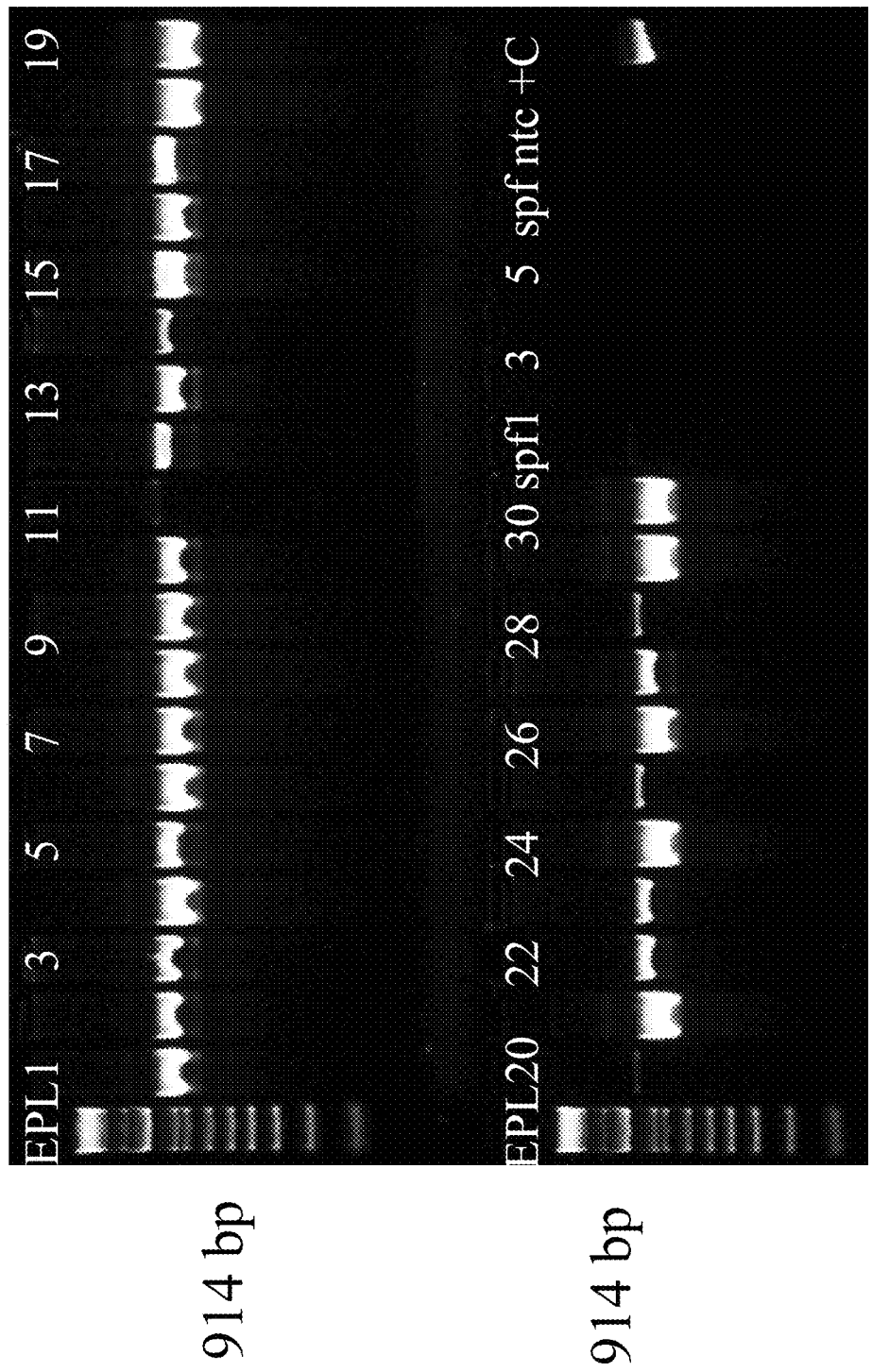
Figure 7C:
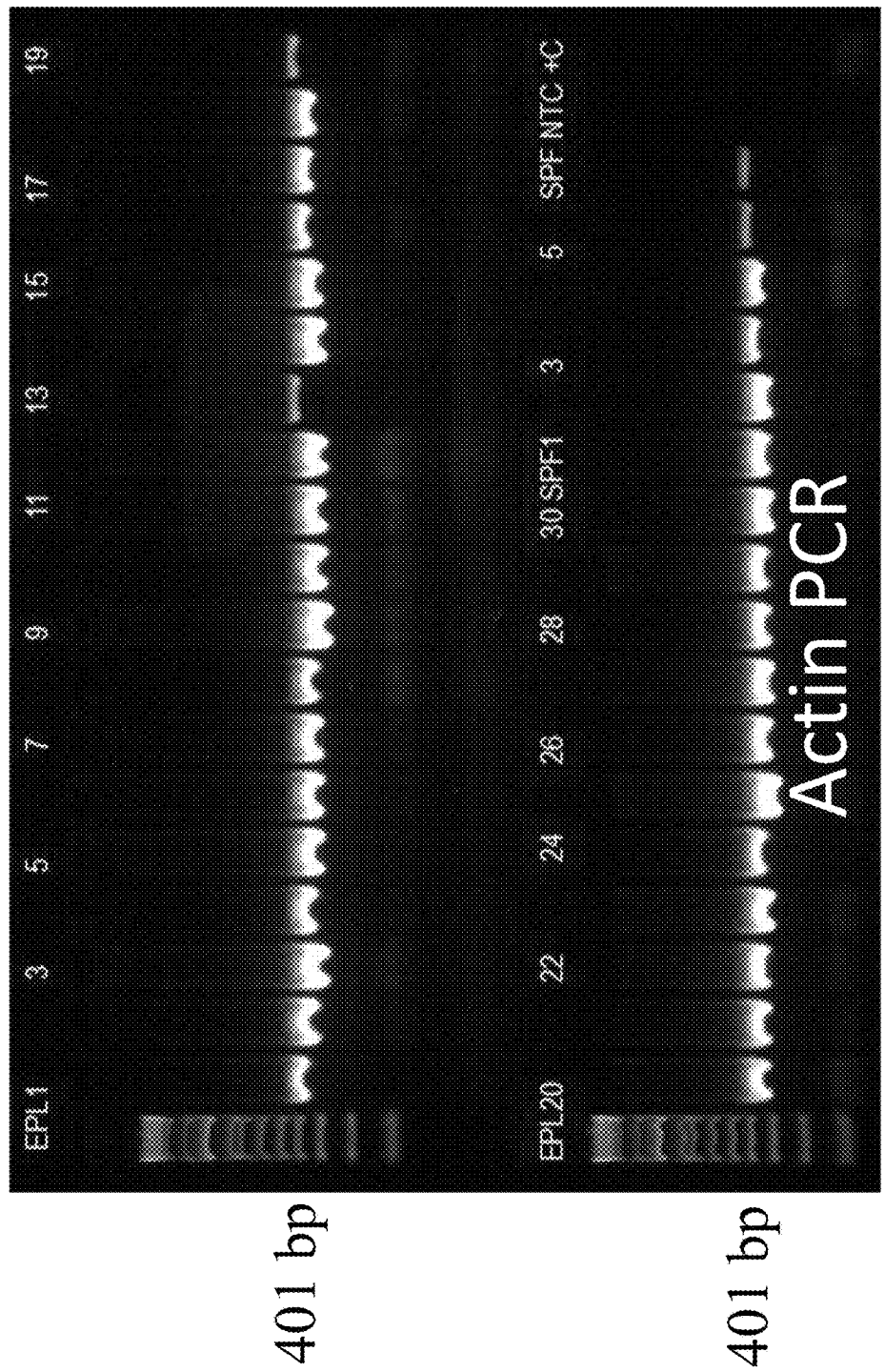

FIGS. 7A-7C show images of representative gels that can demonstrate screening of *Penaeus vannamei* post-larvae for EHP by conventional PCR using primers based on ribosomal DNA small subunit (EHP510) and ATPase transporter gene (atp900). Screening of shrimp (*P. vannamei*) post larvae was done for infection of EHP with EHP510 primers in (FIG. 7A), atp900 primers in (FIG. 7B), and Actin in (FIG. 7C). M—Invitrogen 1 kb DNA ladder, Epl-1-30—EHP-infected independent post larvae, spf1-5 or SPF1-5—Specific pathogen free shrimp, ntc or NTC—Non-template control, +C—respective positive plasmid control.

Table 2 shows the results from testing EHP-infected samples using a previously published conventional PCR method targeting the ribosomal RNA small subunit gene (EHP510-PCR) and an ATPase gene (atp9-PCR, e.g. an ATP-ADP carrier protein gene) as is described elsewhere herein. In case of EHP510-PCR, 3 out of 30 samples (EPL1-30) were not detected (EPL11, EPL20 and EPL26—marked as Not-Detected). By using atp9-PCR, all the EHP-infected samples were successfully detected (marked as Detected). This can demonstrate the specificity of the assays described and provided herein, which is not achieved by currently known detection assays.

TABLE 2

| Samples | EHP510-PCR | atp9-PCR |
|---|---|---|
| EPL1 | Detected | Detected |
| EPL2 | Detected | Detected |
| EPL3 | Detected | Detected |
| EPL4 | Detected | Detected |
| EPL5 | Detected | Detected |
| EPL6 | Detected | Detected |
| EPL7 | Detected | Detected |
| EPL8 | Detected | Detected |
| EPL9 | Detected | Detected |
| EPL10 | Detected | Detected |
| EPL11 | Not Detected | Detected |
| EPL12 | Detected | Detected |
| EPL13 | Detected | Detected |
| EPL14 | Detected | Detected |
| EPL15 | Detected | Detected |
| EPL16 | Detected | Detected |
| EPL17 | Detected | Detected |
| EPL18 | Detected | Detected |
| EPL19 | Detected | Detected |
| EPL20 | Not Detected | Detected |
| EPL21 | Detected | Detected |
| EPL22 | Detected | Detected |
| EPL23 | Detected | Detected |
| EPL24 | Detected | Detected |
| EPL25 | Detected | Detected |
| EPL26 | Not Detected | Detected |
| EPL27 | Detected | Detected |
| EPL28 | Detected | Detected |
| EPL29 | Detected | Detected |
| EPL30 | Detected | Detected |
| Negative Control, SPF1 | Not Detected | Not Detected |
| Negative Control, SPF2 | Not Detected | Not Detected |
| Negative Control, SPF3 | Not Detected | Not Detected |
| Negative Control, SPF4 | Not Detected | Not Detected |
| Negative Control, SPF5 | Not Detected | Not Detected |

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A polymerase chain reaction (PCR) assay capable of specifically detecting *Enterocytozoon hepatopenaei* (EHP) in a nucleic acid sample, the assay comprising:
    specifically amplifying a gene fragment selected from a shrimp ATP-ADP carrier protein gene and optionally an EHP spore wall gene using a polymerase chain reaction (PCR) method, wherein the step of specifically amplifying comprises
        contacting a nucleic acid sample obtained from one or more shrimp, shrimp feed, or shrimp feed ingredient with one or more first primer pairs,
            wherein each of the one or more first primer pairs are configured to specifically amplify one gene fragment from a shrimp ATP-ADP carrier protein gene and optionally an EHP spore wall gene,
            wherein each of the one or more first primer pairs comprises a first oligonucleotide primer and a second oligonucleotide primer, and wherein the each of the one or more first primer pairs are configured to specifically amplify a different gene fragment,
            wherein the first oligonucleotide primer of each of the one or more first primer pairs is a forward direction oligonucleotide primer adapted for PCR amplification of the one gene fragment and specifically binds the gene and wherein the first oligonucleotide primer of at least one of the one or more first primer pairs has a sequence according to SEQ ID NO: 4 and the second oligonucleotide primer of the at least one of the one or more first primer pairs has a sequence according to SEQ ID NO: 5, and wherein the second oligonucleotide primer of each of the one or more first primer pairs is a reverse direction oligonucleotide primer adapted for PCR amplification of the one gene fragment and specifically binds the gene at a different location on the gene than the first oligonucleotide primer, optionally contacting the nucleic acid sample with a second primer pair comprising a third oligonucleotide primer and a fourth oligonucleotide primer, wherein the third oligonucleotide primer is a forward direction oligonucleotide primer adapted for PCR amplification of a fragment of a control gene, wherein the fourth oligonucleotide primer is a reverse direction oligonucleotide primer adapted for PCR amplification of a fragment of the control gene;

detecting the presence or absence of an amplified double stranded DNA fragment of the shrimp ATP-ADP carrier protein gene and optionally the EHP spore wall gene in the nucleic acid sample; and optionally detecting the presence or absence of an amplified double stranded DNA fragment of the control gene in the nucleic acid sample.

2. The assay of claim 1, wherein the PCR method is a real-time PCR method and wherein amplifying further comprises contacting the nucleic acid sample with one or more first oligonucleotide probes adapted for real-time PCR amplification and detection, wherein each first oligonucleotide probe is configured to bind a different gene fragment from an ATP-ADP carrier protein gene fragment and optionally an EHP spore wall gene fragment, wherein each of the one or more first oligonucleotide probes specifically binds a region of the gene DNA fragment that is between a binding region of the first oligonucleotide primer and a binding region of the second oligonucleotide primer in the gene, and wherein the first oligonucleotide probe is coupled to a fluorophore and a quencher molecule; and optionally contacting the nucleic acid sample with a second oligonucleotide probe adapted for real-time PCR amplification and detection, wherein the second oligonucleotide probe specifically binds a region of the control gene that is between a binding region of the third oligonucleotide primer and a binding region the fourth oligonucleotide primer in the control gene, and wherein the second oligonucleotide probe is coupled to a fluorophore and a quencher molecule.

3. The assay of claim 2, wherein the fluorophore of each of the one or more first oligonucleotide probes and the second oligonucleotide probe are responsive to double stranded DNA and are capable of producing a detectable fluorescence upon activation during the step of amplifying in response to double stranded DNA production during amplifying.

4. The assay of claim 2, wherein the fluorophore of at least one of the first oligonucleotide probes is different from the fluorophore of at least one of the second oligonucleotide probes.

5. The assay of claim 1, wherein the control gene is beta actin or shrimp 18S rRNA.

6. The assay of claim 1, wherein detection occurs during the step of amplifying.

7. The assay of claim 1, wherein amplifying further comprises contacting the amplified double stranded DNA fragment of the ATP-ADP carrier protein gene and optionally the amplified double stranded DNA fragment of the EHP spore wall gene with a detectable dye molecule that binds double stranded DNA and optionally contacting the amplified double stranded DNA fragment of the control gene with a detectable dye molecule that binds double stranded DNA.

8. The assay of claim 7, wherein contacting the amplified double stranded DNA fragment of the ATP-ADP carrier protein gene and optionally the EHP spore wall gene with a detectable dye molecule that binds double stranded DNA occurs during the step of amplifying.

9. The assay of claim 1, wherein amplifying the ATP-ADP carrier protein gene and optionally amplifying the EHP spore wall gene and amplifying the control gene is carried out in the same PCR reaction.

10. The assay of claim 1, wherein amplifying the ATP-ADP carrier protein gene and optionally amplifying the EHP spore wall gene and the amplifying the control gene is carried out in the different PCR reactions.

11. The assay of claim 1, wherein there is no detectable non-specific amplification of a PCR product.

12. The assay of claim 1, wherein the assay does not detect a non-EHP organism selected from the group consisting of: *Enterocytospora artemiae*, acute hepatopancreatic necrosis disease (AHPND), infectious hypodermal and hematopoietic necrosis virus (IHHNV), necrotizing hepatopancreatitis (NHP), white spot syndrome virus (WSSV), infectious myonecrosis virus (IMNV), *Penaeus vannamei* nodavirus (PvNV), Taura syndrome virus (TSV), yellowhead disease (YHV), and combinations thereof.

* * * * *